United States Patent
Bittler et al.

(10) Patent No.: US 6,288,051 B1
(45) Date of Patent: Sep. 11, 2001

(54) 7 α-(5-METHYLAMINOPENTYL)-ESTRATRIENES, PROCESS FOR THEIR PRODUCTION, PHARMACEUTICAL PREPARATIONS THAT CONTAIN THESE 7 α(5-METHYLAMINOPENTYL)-ESTRATRIENES AS WELL AS THEIR USE FOR THE PRODUCTION OF PHARMACEUTICAL AGENTS (75) Inventors: Dieter Bittler; Rolf Bohlmann; Nikolaus Heinrich; Jorg Kroll; Gerhard Sauer; Yukishige Nishino; Karsten Parczyk; Martin Schneider; Christa Hegelehartung; Rosemarie Lichtner, all of Berlin (DE)

(73) Assignee: Schering Aktiengesellschaft (DE)

( * ) Notice: Subject to any disclaimer, the term of this patent is extended or adjusted under 35 U.S.C. 154(b) by 0 days.

(21) Appl. No.: 09/417,765

(22) Filed: Oct. 14, 1999

Related U.S. Application Data (63) Continuation of application No. 09/194,120, filed as application No. PCT/EP97/02718 on Nov. 4, 1998, now abandoned.

(30) Foreign Application Priority Data

May 24, 1996 (DE) ............................................. 196 22 457

(51) Int. Cl.$^7$ ............................... A61K 31/56; C07J 5/00

(52) U.S. Cl. .......................... 514/182; 514/182; 552/576

(58) Field of Search ............................. 552/576; 514/182

(56) References Cited

FOREIGN PATENT DOCUMENTS 4218743   12/1993  (DE) .
138504    4/1985   (EP) .

OTHER PUBLICATIONS

Bittler et al. (CA 128:34925, abstract of DE 19622457) 1996.*

* cited by examiner

Primary Examiner—Sabiha Qazi (57) ABSTRACT

This invention describes the new 7α-(5-methylaminopentyl)-estratrienes of general formula I

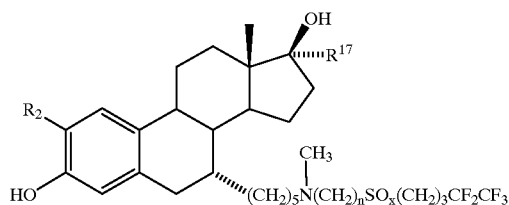

in which R$^2$ stands for a hydrogen or fluorine atom,

R$^{17}$ stands for a hydrogen atom, a methyl or ethinyl group, n stands for 2, 3 or 4, and x stands for 0, 1 or 2.

The new compounds are strong, pure antiestrogens and can be used for the production of pharmaceutical agents for treatment of estrogen-dependent diseases, for example, breast cancer, endometrial carcinoma, prostatic hyperplasia, anovulatory infertility and melanoma.

16 Claims, 5 Drawing Sheets

Antiuterotrophic Action in Infantile Rats s.c.

□ 7α-[9-(4,4,5,5,5-Pentafluoropentylsulfinyl)-n-nonyl]-estra-1,3,5(10)-triene-3,17β-diol ○ 7α-{5-[N-Methyl-N-3-(4,4,5,5,5-pentafluoropentylthio)-propylamino]-pentyl}-estra-1,3,5(10)-triene-3,17β-diol Relative levels of effectiveness 5,4

FIG. 1

Antiuterotrophic Action in Infantile Rats p.o.

□ 7α-[9-(4,4,5,5,5-Pentafluoropentylsulfinyl)-n-nonyl]-estra-1,3,5(10)-triene-3,17β-diol ○ 7α-{5-[N-Methyl-N-3-(4,4,5,5,5-pentafluoropentylthio)-propylamino]-pentyl}-estra-1,3,5(10)-triene-3,17β-diol Relative levels of effectiveness 4,7

7 α-(5-METHYLAMINOPENTYL)-ESTRATRIENES, PROCESS FOR THEIR PRODUCTION, PHARMACEUTICAL PREPARATIONS THAT CONTAIN THESE 7 α (5-METHYLAMINOPENTYL)-ESTRATRIENES AS WELL AS THEIR USE FOR THE PRODUCTION OF PHARMACEUTICAL AGENTS

This is a continuation of application Ser. No. 09/194,120 filed Nov. 4, 1998 now abandoned which is a 371 of PCT/EP97/02718 filed May 26, 1997.

This invention relates to 7α-(5-methylaminopentyl)-estratrienes of general formula I in which
R$^2$ stands for a hydrogen or fluorine atom,
R$^1$ stands for a hydrogen atom, a methyl or ethinyl group,
n stands for 2, 3 or 4, and
x stands for 0, 1 or 2.

This invention especially relates to the estratrienes
7α-{5-[N-Methyl-N-3-(4,4,5,5,5-pentafluoropentylthio)-propylamino]-pentyl}-estra-1,3,5(10)-triene-3,17β-diol
17α-methyl-7α-{5-[N-methyl-N-3-(4,4,5,5,5-pentafluoropentylthio)-propylamino)]-pentyl}-estra-1,3,5(10)-triene-3,17β-diol
17α-ethinyl-7α-{5-[N-methyl-N-3-(4,4,5,5,5-pentafluoropentylthio)-propylamino]-pentyl}-estra-1,3,5(10)-triene-3,17β-diol
7α-{5-[N-methyl-N-2-(4,4,5,5,5-pentafluoropentanesulfonyl)-ethylamino]-pentyl}-estra-1,3,5(10)-triene-3,17β-diol
7α-{5-[N-methyl-N-3-(4,4,5,5,5-pentafluoropentanesulfonyl)-propylamino]-pentyl}-estra-1,3,5(10)-triene-3,17β-diol
2-fluoro-7α-{5-[N-methyl-N-3-(4,4,5,5,5-pentafluoropentylthio)-propylamino]-pentyl}-estra-1,3,5(10)-triene-3,17β-diol
7α-{5-[N-methyl-N-3-(4,4,5,5,5-pentafluoropentanesulfinyl)-propylamino]-pentyl}-estra-1,3,5(10)-triene-3,17β-diol
2-fluoro-17α-methyl-7α-{5-[N-methyl-N-3-(4,4,5,5,5-pentafluoropentylthio)-propylamino]-pentyl}-estra-1,3,5(10)-triene-3,17β-diol
2-fluoro-7α-{5-[N-methyl-3-(4,4,5,5,5-pentafluoropentanesulfinyl)-propylamino]-pentyl}-estra-1,3,5(10)-triene-3,17β-diol
2-fluoro-17α-methyl-7α-{5-[N-methyl-N-3-(4,4,5,5,5-pentafluoropentanesulfonyl)-propylamino]-pentyl}-estra-1,3,5(10)-triene-3,17β-diol
7α-{5-[N-methyl-N-4-(4,4,5,5,5-pentafluoropentylthio)-butylamino]-pentyl}-estra-1,3,5(10)-triene-3,17β-diol
7α-{5-[N-methyl-N-4-(4,4,5,5,5-pentafluoropentanesulfinyl)-butylamino]-pentyl}-estra-1,3,5(10)-triene-3,17β-diol
17α-methyl-7α-{5-[N-methyl-N-3-(4,4,5,5,5-pentafluoropentanesulfinyl)-propylamino]-pentyl}-estra-1,3,5(10)-triene-3,17β-diol
17α-methyl-7α-{5-[N-methyl-N-3-(4,4,5,5,5-pentafluoropentanesulfonyl)-propylamino]-pentyl}-estra-1,3,5(10)-triene-3,17β-diol
17α-ethinyl-7α-{5-[N-methyl-N-3-(4,4,5,5,5-pentafluoropentanesulfonyl)-propylamino]-pentyl}-estra-1,3,5(10)-triene-3,17β-diol The compounds of general formula I represent compounds with very strong antiestrogenic action.

Compounds with antiestrogenic properties, i.e., substances with inhibiting actions relative to estrogens, have already been described extensively.

As the compounds that come closest structurally to the compounds in question here of general formula I, the steroid derivatives that are described in EP-A 0 138 504 can be considered, and of the latter especially 7α-[9-(4,4,5,5,5-pentafluoropentanesulfinyl)-nonyl]-estra-1,3,5(10)-triene-3,17β-diol (page 58, penultimate compound). This compound is currently under clinical development for hormone-dependent tumors (breast cancer) and represents the compound that is best known at this time, i.e., the one with the strongest antiestrogenic activity, of these steroid derivatives.

The compounds according to the invention are pure antiestrogens with stronger, several times better, antiestrogenic action than 7α-[9-(4,4,5,5,5-pentafluoropentanesulfinyl)-nonyl]-estra-1,3,5(10)-triene-3,17β-diol. This holds true for several in vitro and in vivo criteria, but especially for oral action in vivo on rats.

Pharmaceutical compositions that contain sex steroid inhibitors and exhibit a steroidal skeleton, which exhibits a 7α-side chain with the simultaneous presence of at least one other substituent, are the object of EP-A 0 367 576.

Other steroidal antiestrogens, which carry an 11β-phenyl radical, are described in EP-AS 0 384 842 and 0 629 635.

A considerable number of the most varied compounds—i.a., those of steroidal origin and those with a 2-phenylindole skeleton—which act as antiestrogens and/or suppress the estrogen biosynthesis, are disclosed in WO 93/10741.

The compounds of general formula I according to this application are distinguished in comparison to the already known steroid derivatives according to EP-A 0 138 504 by novel side chains on carbon atom 7 of the steroid skeleton. This structural modification results in especially greatly antiestrogenically active compounds.

The antiestrogenic action of the compounds according to the invention was determined in transactivation assays [Demirpence, E.; Duchesne M.-J.; Badia, E.; Gagne, D. and Pons, M.: MVLN Cells: A Bioluminescent MCF-7-Derived Cell Line to Study the Modulation of Estrogenic Activity; J. Steroid. Molec. Biol. Vol. 46, No. 3, 355–364 (1993) as well as Berry, M.; Metzeger D.; Chambon, P.: Role of the Two Activating Domains of the Estrogen Receptor in the Cell-type and Promoter-context Dependent Agonistic Activity of the Anti-estrogen 4-Hydroxytamoxifen; The EMBO Journal Vol. 9, 2811–2818 (1990)].

The antiproliferative activity of the new compounds in breast neoplasm cell lines is greater than that of 7α-[9-4,4,5,5,5-pentafluoropentanesulfinyl)-nonyl]-estra-1,3,5(10)-triene-3,17β-diol.

The IC$_{50}$ values for the new compounds lie in the nanomolar range. In the HeLa cell line as well as the MVLN cell line, the following IC$_{50}$ values are produced for the compounds of Examples 1 to 6 as well as for reference compound 7α-[9-(4,4,5,5,5-pentafluoropentanesulfinyl)-nonyl]-estra-1,3,5(10)-triene-3,17β-diol (execution of the test according to the above-indicated bibliographic references). The HeLa cells are transfixed with human estrogen receptor-expression vector (HEGO) and Vit-TK-CAT reporter genes, and the MVLN cells are transfixed with reporter gene Vit-TK-LUC:

| | $IC_{50}$ [nM] | |
|---|---|---|
| Compound | HeLa cells | MVLN cells |
| Example 1 | 0.3 | 1.0 |
| Example 2 | 0.2 | 0.6 |
| Example 3 | 1.0 | 0.6 |
| Example 4 | 0.16 | 1.3 |
| Example 5 | 0.3 | 0.66 |
| Example 6 | 0.1 | 1.0 |
| Reference: 7α-[9-(4,4,5,5,5-pentafluoro-pentanesulfinyl)-nonyl]-estra-1,3,5(10)-triene-3,17β-diol | 0.5 | 6.0 |

The compounds have an inhibiting action on the growth of hormone-dependent tumor cells; they especially inhibit the growth of estrogen-dependent human breast neoplasm cells (MCF-7).

In-vivo tests also impressively confirm the superiority-of the compounds according to the invention compared to 7α-[9-(4,4,5,5,5-pentafluoropentanesulfinyl)-nonyl]-estra-1,3,5(10)-triene-3,17β-diol. The tests described below were carried out:

1. Uterus growth test in infantile rats, s.c. and p.o. (test for antiestrogenic action)
2. Tumor tests of anti-tumor effect on hormone-dependent breast cancer)
    2.1 MXT breast neoplasm in mice
    2.2 DMBA*-induced breast cancer in rats
    2.3 NNMU⁺-induced breast cancer in rats
        *=dimethylbenzanthracene
        ⁺=N-nitroso-N-methylurea 1. Uterus Growth Test in Infantile Rats (Antiestrogenic Action)

Principle of the Method

In rodents, the uterus reacts to the administration of estrogens with an increase in weight (both proliferation and water retention). This growth is to be inhibited in a dose-dependent-manner by simultaneous administration of compounds with an antiestrogenic action.

Execution of the Test

Animals:

Infantile female rats at a weight of 35–45 g at the beginning of the test, 5–6 animals per dose.

Formulation and Administration of the Substances:

Both for s.c. and for p.o. administration, the substances are dissolved in 1 part of ethanol (E) and made up with 9 parts of peanut oil (EÖ).

Test Batch

Young rats that have just been weaned from their mothers are delivered one day before the beginning of treatment for acclimatization and are immediately supplied with food—still in the animal cage. The treatment is then carried out once a day for 3 days in combination with 0.5 μg of estradiol benzoate (EB). EB is always administered subcutaneously (s.c.), while the test substance is administered either s.c. or p.o. (perorally). 24 hours after the last administration, the animals are weighed and killed, and the uteri are removed. The wet weights (without contents) are determined from the prepared uteri.

Controls

Negative control: vehicle (E/EÖ), 0.2 ml/animal/day
Positive control: 0.5 μg of EB/0.1 ml/animal/day Analysis For each group, the average values with standard deviation (X+SD), as well as the significance of the differences compared to the control group (EB) in the Dunnett Test ($p<0.05$), are determined from the relative organ weights (mg/100 g of body weight). The calculation of inhibition (in %) compared to the EB control is done with a program. The relative effects of the test substances are determined by covariance and regression analysis.

2. Tumor Tests 2.1. Tumor-Inhibiting Effect on Hormone-Dependent 1XT (+)-Breast Cancer in Mice Principle of the Method The MXT(+)-breast cancer is an estrogen- and progesterone receptor-positive tumor that was originally produced by induction with urethane and is then transplanted onward in series. Growth can be inhibited by ovariectomy and antiestrogens. This model is therefore very well suited for studying the tumor-inhibiting action of endocrinotherapeutic agents.

Execution of the Test

Animal Material

Adult, female BDFI-mice (7–10 weeks old; weight 18–21 g).

Standard care conditions.

Formulation and Administration of Test Substances

The test substances are dissolved in ethanol+peanut oil (1+9), and the one-time dose is administered at a volume of 0.1 ml s.c. In the case of oral administration, the test substance is dissolved in ethanol+peanut oil (1+9), and the daily dose is administered at a volume of 0.1 ml. The treatment begins either immediately after tumor implantation or 2–3 weeks thereafter (treatment of established tumors). The maximum treatment time is 12 weeks.

Tumor Strain Care

To this end, tumor fragments with an edge length of about 2 mm are implanted s.c. inguinally bilaterally in normal mice with a lumbar puncture needle. Depending on the growth of the tumor, production of a new strain is begun every 5–6 weeks.

Test Batch

The tumors are removed under aseptic conditions from at least 4 tumors of the strain production and pooled, cut into pieces with an edge length of about 2 mm, and implanted in the animals as described above. The mice are randomized at 9–10 animals per group. One group is ovariectomized for control of hormone-dependence. Tumor growth is determined by ascertaining the tumor surface area with the aid of a sliding gauge. The tumor surface area is calculated from the product of the longest diameter and the tumor diameter that is perpendicular to said longest diameter. At the end of the test, the animals are killed, and the tumors as well as optionally uteri and ovaries are dissected and weighed.

Analysis

Average values ±SE of tumor surface areas are determined. The course of the growth of the tumors is plotted graphically.

The statistical analysis is carried out with the Dunnett test.

2.2. Influencing Tumor Growth in the DMBI* Model in Rats (DMBA Tumor Model)

*9,10-Dimethyl-1,2-benanthracene

Biological Principle

The growth of the DMBA-induced breast neoplasm of rats is largely dependent on estrogens and prolactin. Active antiestrogens, antigestagens, and aromatase inhibitors result in the inhibition of tumor growth, and substances that have antigonadotropic and androgenic properties also exert a tumor-inhibiting action.

Animal Material

45–47-day-old female rats (Sprague-Dawley, breeder ZiH or Möllegard), 8–10 animals per group.

Test Batch

The animals receive 10 mg of DMBA orally on a one-time basis. Then, the animals are examined weekly by palpation for tumor development. Six to 10 weeks after DNBA treatment, approximately 1 to 10 tumors develop per animal. The tumor size is determined once a week with the aid of a sliding gauge. If at least one tumor has reached a specific size (150 mm² of tumor surface area), an ovariectomy is performed on the animals, or the treatment of the animals with the test substance begins. The treatment is carried out in most cases daily for a period of about 28 days (for details on execution, see Test Plan). The tumor size is subsequently determined once a week.

Analysis

The total tumor size per animal is determined before the beginning of treatment (initial values). For each group, the average values of the percentage changes of the tumor size relative to the initial value are then calculated. In addition, the percentage of animals per group is determined, whose tumors in each case: (1) have totally disappeared (total regression); partially disappeared (partial regression); (3) are unchanged (no change); or (4) are further enlarged (enlargement).

The values that are found are tested for significance in the Dunnett Test and are plotted graphically.

2.3 Influencing of Tumor Growth in the NMU⁺ Model in Rats (MM Tumor Model)

⁺N-Methyl-N-nitrosourea

Biological Principle

The growth of the NMU-induced breast neoplasm of rats is largely dependent on estrogens and, in contrast to the DMBA tumor model, less on prolactin. Active antiestrogens, aromatase inhibitors, and antigestagens lead to the inhibition of tumor growth. Substances with antigonadotrophic properties also exert a tumor-inhibiting action.

Animal Material

Female rats (Sprague-Dawley)
55 d old (±3 d)
8–10 animals per group

Type of Administration

NMU=i.v., test substance: s.c./p.o.

Vehicle Volumes

| p.o. = | 0.1 or 0.2 ml/100 g/d | in ethanol + peanut oil (1 + 9) |
| s.c. = | 0.1 ml/100 g/d | in ethanol + peanut oil (1 + 9) |
| NMU = | 50 mg/kg/d | 1.5 ml/200 g (0.9% NaCl/0.085% Myrj-53) |

Test Batch

The animals receive 50 mg/kg of NMU i.v. on a one-time basis. Then, the animals are examined once a week by palpation for tumor development. About 6–8 weeks after NMU treatment, one or more tumors develop per animal. At a minimum size of 150 mm²/tumor/animal, daily treatment (7× a week) begins with the test substance, and the determination of body weight+tumor size is done (with the aid of a sliding gauge) (1×/week).

The values that are found are tested for significance in the Dunnett Test and are plotted graphically.

Test Results

1. Antiuterotrophic Action in Infantile Rats

Figure 1:
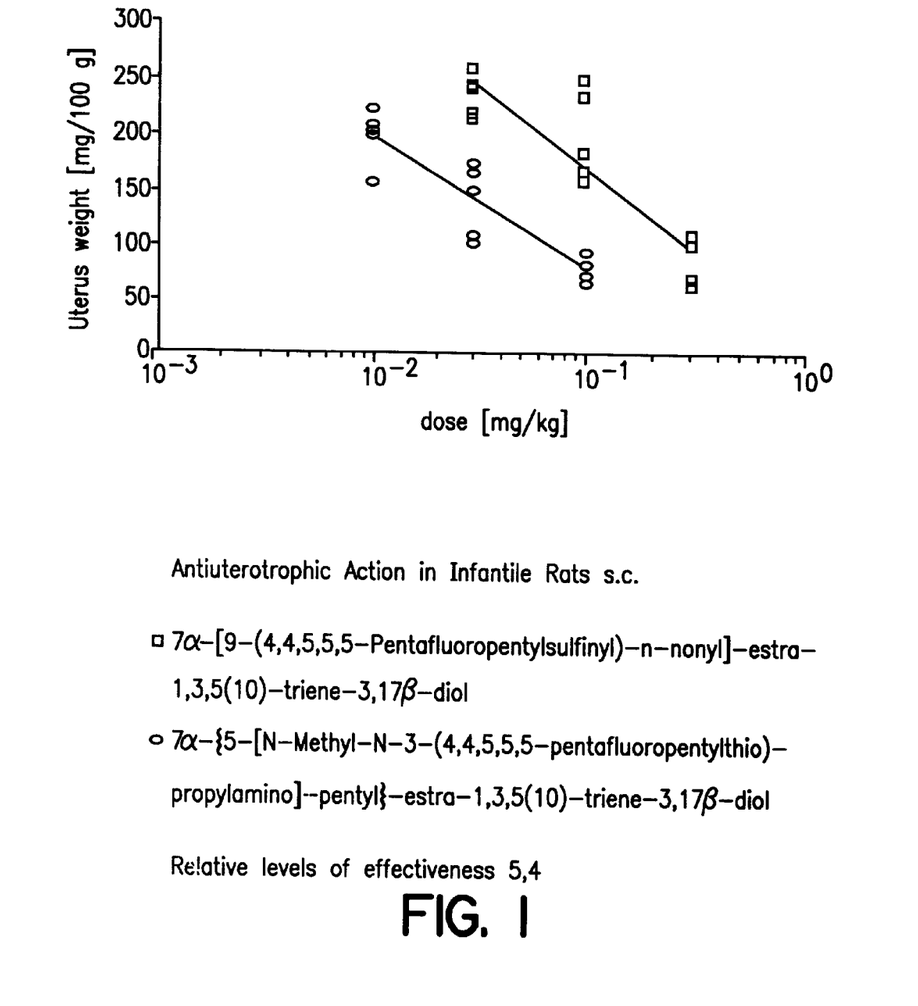
Figure 2:
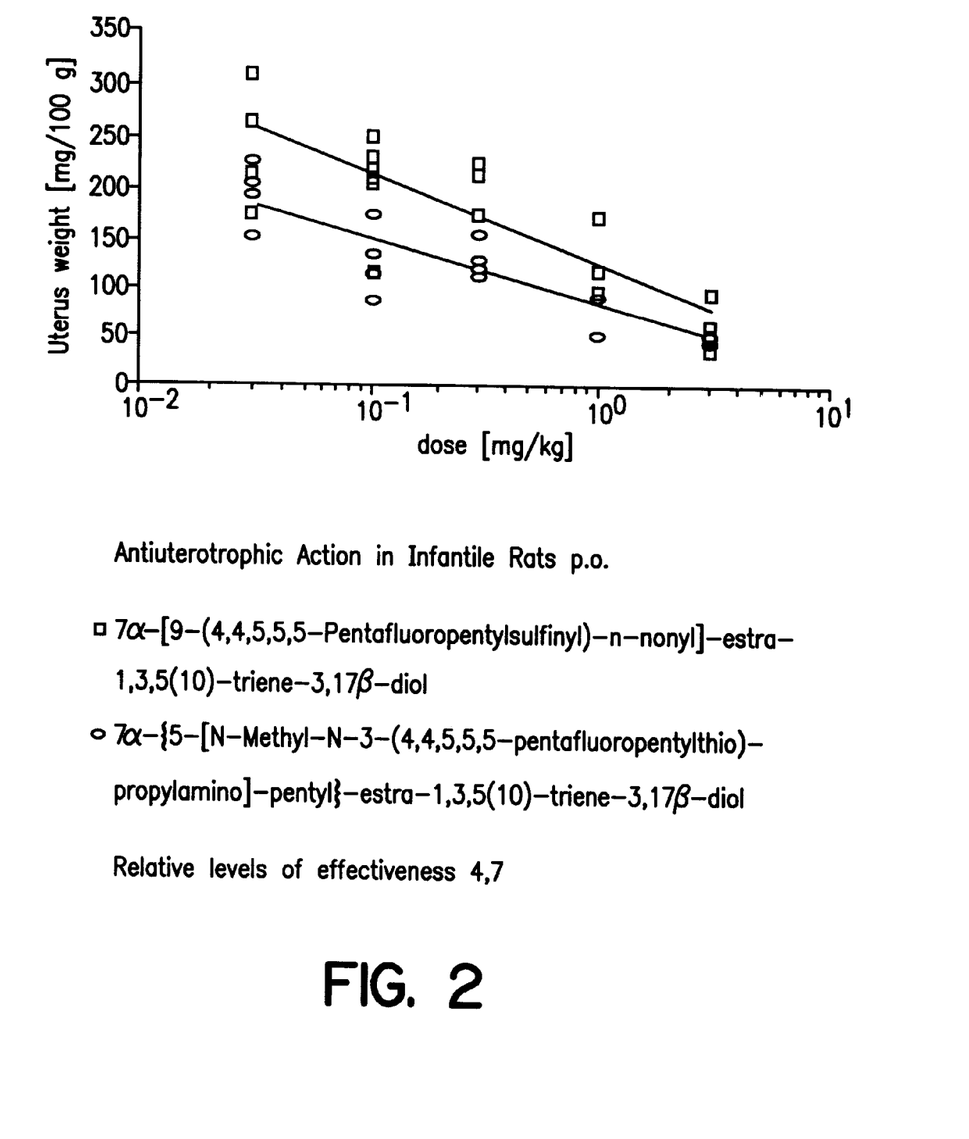

In the case of subcutaneous or oral administration, 7α-{5-[N-methyl-N-3-(4,4,5,5,5-pentafluoropentylthio)-propylamino]-pentyl}-estra-1,3,5(10)-triene-3,17β-diol is, respectively, 5.4 times or 4.7 times more strongly antiestrogenically active than 7α-[9-(4,4,5,5,5-pentafluoropentanesulfinyl)-nonyl]-estra-1,3,5(10)-triene-3, 17β-diol (FIGS. 1 and 2). These differences in action are highly significant.

Figure 3:
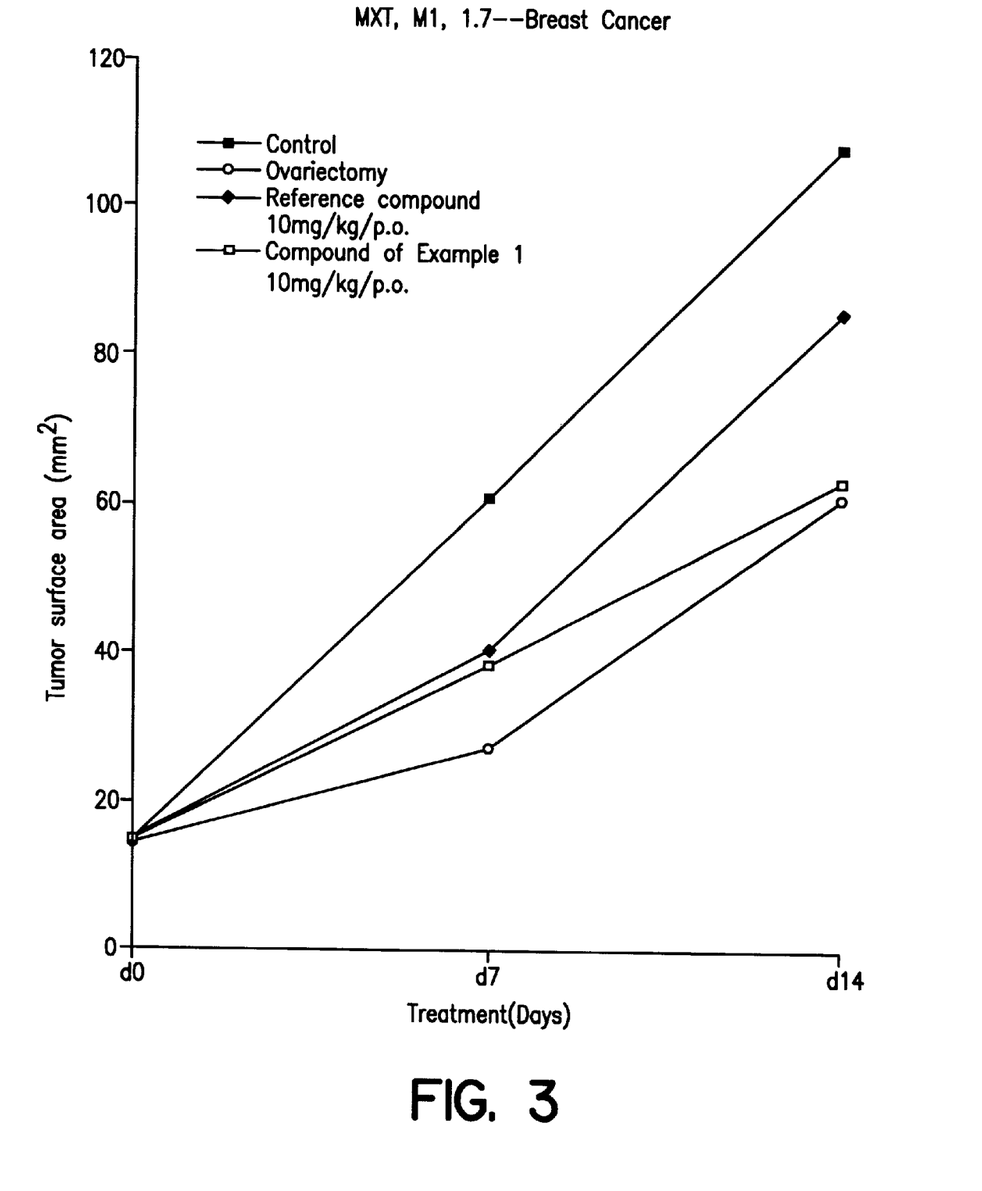

2. Antitumor Effect on Hormone-dependent Breast Cancer 2.1. MXT Breast Neoplasm in Mice After 14 days of treatment at an oral dose of 10 mg/kg/day, 7α-{5-[N-methyl-N-3-(4,4,5,5,5-pentafluoropentylthio)-propylamino]-pentyl}-estra-1,3,5(10)-triene-3,17β-diol inhibits tumor growth as strongly as an ovariectomy (FIG. 3). In this case, 7α-{5-[N-methyl-N-3-(4,4,5,5,5-pentafluoropentylthio)-propylamino]-pentyl}-estra-1,3,5(10)-triene-3,17β-diol is more strongly active than 7α-[9-(4,4,5,5,5-pentafluoropentanesulfinyl)-nonyl]-estra-1,3,5(10)-triene-3,17β-diol.

2.2. DMBA-induced Breast Cancer in Rats

Figure 4:
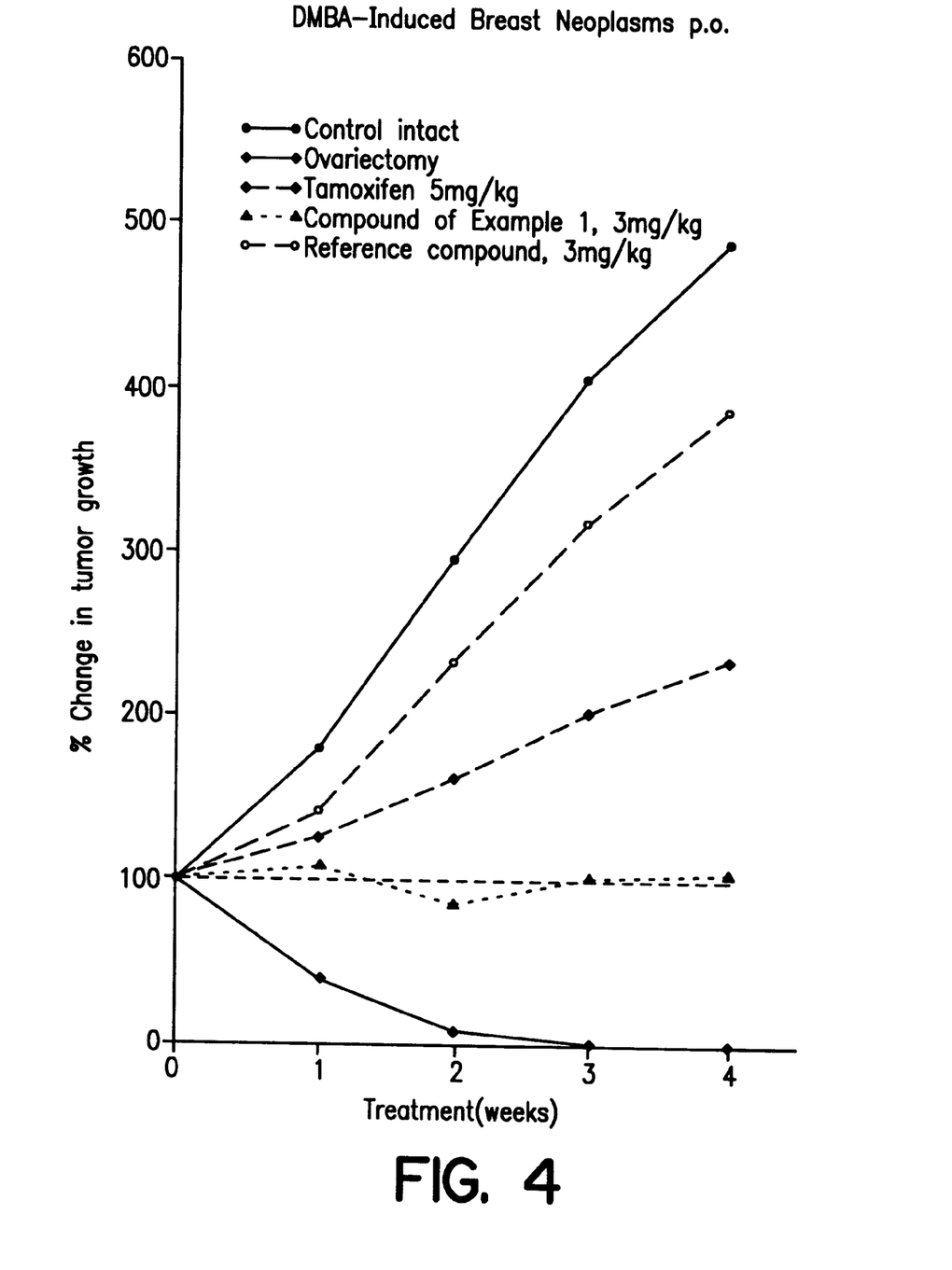

At an oral dose of 3 mg/kg/day, 7α-{5-[N-methyl-N-3-(4,4,5,5,5-pentafluoropentylthio)-propylamino]-pentyl}-estra-1,3,5(10)-triene-3,17β-diol completely inhibits tumor growth (no growth), while 7α-[9-(4,4,5,5,5-pentafluoropentanesulfinyl)-nonyl]-estra-1,3,5(10)-triene-3, 17β-diol exerts only a slight action at the same dose (FIG. 4). 7α-{5-[N-Methyl-N-3-(4,4,5,5,5-pentafluoropentylthio)-propylamino]-pentyl}-estra-1,3,5(10)-triene-3,17β-diol is even more strongly active than tamoxifen (TAM). In this case, an ovariectomy results in total tumor remission.

2.3. NMU-induced Breast Cancer in Rats

Figure 5:
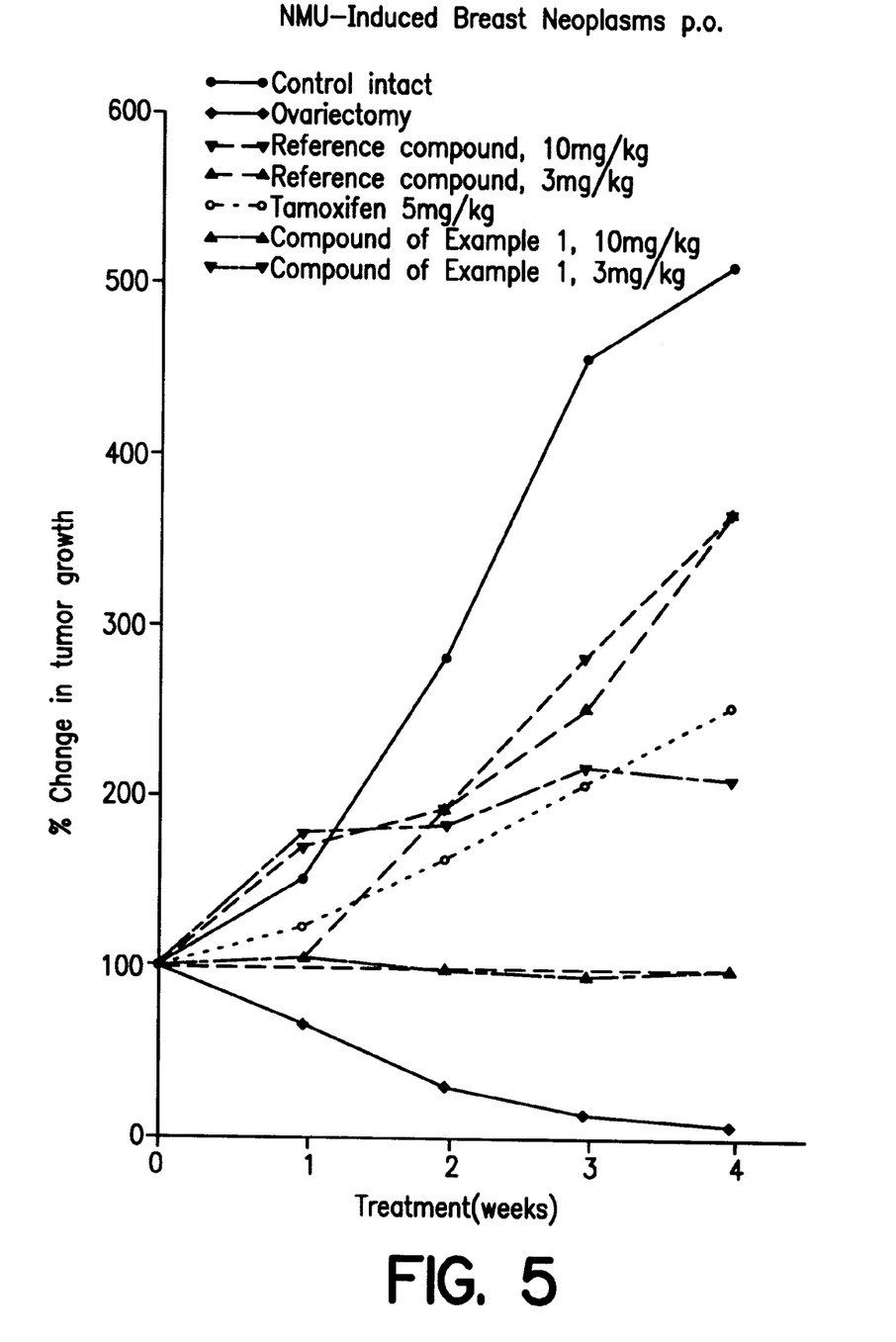

7α-{5-[N-Methyl-N-3-(4,4,5,5,5-pentafluoropentylthio)-propylamino]-pentyl}-estra-1,3,5(10)-triene-3,17β-diol, orally administered, inhibits tumor growth in a dose-dependent manner (FIG. 5). At a dose of 10 mg/kg/day, 7α-{5-[N-methyl-N-3-(4,4,5,5,5-pentafluoropentylthio)-propylamino]-pentyl}-estra-1,3,5(10)-triene-3,17β-diol results in complete inhibition of tumor growth. 7α-{5-[N-Methyl-N-3-(4,4,5,5,5-pentafluoropentylthio)-propylamino]-pentyl}-estra-1,3,5(10)-triene-3,17β-diol is clearly more strongly active than 7α-[9-(4,4,5,5,5-pentafluoropentanesulfinyl)-nonyl]-estra-1,3,5(10)-triene-3, 17β-diol.

The compounds according to the invention thus are suitable for treatment of estrogen-dependent diseases, for example, breast cancer, endometrial carcinoma, prostatic hyperplasia, anovulatory infertility and melanoma.

The invention also relates to pharmaceutical preparations, which contain at least one compound of general formula I, and the use of these compounds for the production of pharmaceutical agents, especially for treating estrogen-dependent diseases and tumors.

The compounds according to the invention are suitable for the production of pharmaceutical compositions and preparations. The pharmaceutical compositions or pharmaceutical agents contain as active ingredient one or more of the compounds according to the invention, optionally in a mixture with other pharmacologically or pharmaceutically active substances. The production of the pharmaceutical agents is carried out in a known way, whereby the known and commonly used pharmaceutical adjuvants as well as other commonly used vehicles and diluents can be used.

As such vehicles and adjuvants, for example, those are suitable which are recommended or indicated in the following bibliographic references as adjuvants-for pharmaceutics, cosmetics and related fields: Ullmans Encyklopädie der technischen Chemie [Ullman's Encyclopedia of Technical Chemistry], Volume 4 (1953), pp. 1 to 39; Journal of Pharmaceutical Sciences, Volume 52 (1963), pp. 918 and ff.; H. v. Czetsch-Lindenwald, Hilfsstoffe für Pharmazie und angrenzende Gebiete [Adjuvants for Pharmaceutics and Related Fields]; Pharm. Ind. Number 2, 1961, pp. 72 and ff.; Dr. H. P. Fiedler, Lexikon der Hilfsstoffe für Pharmazie, Kosmetik und angrenzende Gebiete [Encyclopedia of Adjuvants for Pharmaceutics, Cosmetics and Related Fields], Cantor KG. Aulendorfin Wurtemberg 1971.

The compounds can be administered preferably orally or else parenterally, for example, intraperitoneally, intramuscularly, subcutaneously or percutaneously. The compounds can also be implanted in tissue. The amount of the compounds to be administered varies within a wide range and can cover any effective amount. Depending on the condition to be treated and the type of administration, the amount of administered compound is 0.1–25 mg/kg of body weight, preferably 0.5–5 mg/kg of body weight, per day. In humans, this corresponds to a daily dose of 5 to 1250 mg.

For oral administration, capsules, pills, tablets, coated tablets, etc., are suitable. In addition to the active ingredient, the dosage units can contain a pharmaceutically compatible vehicle, such as, for example, starch, sugar, sorbitol, gelatin, lubricant, silicic acid, talc, etc. The individual dosage units for oral administration can contain, for example, 5 to 500 mg of active ingredient.

For parenteral administration, the active ingredients can be dissolved or suspended in a physiologically compatible diluent. As a diluent, very frequently oils with or without the addition of a solubilizer, a surfactant, a suspending agent or emulsifier are used. Examples of oils that are used are olive oil, peanut oil, cottonseed oil, soybean oil, castor oil and sesame oil.

The compounds can also be used in the form of a depot injection or an implant preparation, which can be formulated so that a delayed release of active ingredient is made possible.

Implants can contain, as inert materials, for example, biodegradable polymers or synthetic silicones, such as, for example, silicone rubber. In addition, the active ingredients can be added to, for example, a patch, for percutaneous administration.

The compounds according to the invention can be produced as described below. The following examples are used for a more detailed explanation of the invention. By an analogous approach using reagents like those in the data contained in the examples, all compounds of general formula I can be obtained.

EXAMPLES

Example 1

7α-{5-[N-Methyl-N-3-(4,4,5,5,5-pentafluoropentylthio)-propylamino]-pentyl}-estra-1,3,5(10)-triene-3,17β-diol a) 17β-Acetoxy-7α(5-tert-butyl-dimethylsilyloxypentyl)-estr-4-en-3-one In 200 ml of absolute THF, 22.9 g of Mg chips with 261 g of 1-bromo-5-tert-butyl-dimethylsilyloxypentane [Tetrahedron Letters 23, 1982, 40, 4147–4150], dissolved in 250 ml of absolute THF, is reacted to form the Grignard reagent. 92.9 g of copper(I) iodide is added to this solution, cooled to −20° C., under a nitrogen stream, and then 73.5 g of 17β-acetoxyestra-4,6-dien-3-one [J. Am. Chem. Soc. 80, 1958, 2596–2597], dissolved in 300 ml of absolute THF, is added in drops within one hour. For working-up, 61.2 ml of acetic acid is added in drops, the reaction mixture is diluted with ethyl acetate, washed with saturated ammonium chloride solution, water and sodium bicarbonate solution and dried. The residue that is obtained after the concentration by evaporation is chromatographed on silica gel. 48 g of 17β-acetoxy-7α-(5-tert-butyl-dimethylsilyloxypentyl)-estr-4-en-3-one is obtained.

b) 17β-Acetoxy-7α-(5-hydroxypentyl)-estr-4-en-3-one

A solution of 48 g of 17β-acetoxy-7α-(5-tert-butyl-dimethylsilyloxypentyl)-estr-4-en-3-one in 350 ml of methanol is allowed to stand with 35 ml of 8 vol % sulfuric acid for 30 minutes at room temperature. The solution is diluted with diethyl ether, washed neutral with water, and dried. After the concentration by evaporation, 37.7 g of 17β-acetoxy-7α-(5-hydroxypentyl)-estr-4-en-3-one is obtained as an oil.

c) 17β-Acetoxy-7α-(5-acetoxypentyl)-estr-4-en-3-one

A solution of 37.7 g of 17β-acetoxy-7α-(5-hydroxypentyl)-estr-4-en-3-one in 160 ml of pyridine is slowly mixed with 80 ml of acetic anhydride and stirred for 16 hours at 25° C. Then, it is diluted with ethyl acetate, and the organic phase, after washing with sodium bicarbonate solution, is dried and concentrated by evaporation. The residue is chromatographed on silica gel, and 26.6 g of 17β-acetoxy-7α-(5-acetoxypentyl)-estr-4-en-3-one is obtained as an oil. $[\alpha]_D^{22}$=+20.00 (c=0.51% in chloroform)

d) 17β-Acetoxy-7α-(5-acetoxypentyl)-estra-1,3,5(10)-trien-3-ol

A solution of 5.18 g of lithium bromide and 26.73 g of copper(II) bromide in 260 ml of acetonitrile is added in drops to a solution of 26.6 g of 17β-acetoxy-7α-(5-acetoxypentyl)-estr-4-en-3-one in 260 ml of acetonitrile, heated to 80° C., within 30 minutes while being stirred. After the addition is completed, the reaction solution is cooled, diluted with diethyl ether, washed with water and sodium bicarbonate solution and dried. The residue that is obtained after the concentration by evaporation is chromatographed on silica gel, and 21.3 g of 17β-acetoxy-7α-(5-acetoxypentyl)-1,3,5(10)-estratrien-3-ol is obtained as an oil. $[\alpha]_D^{22}$=+28.9° (c=0.535% in chloroform)

e) 17β-Acetoxy-7α-(5-acetoxypentyl)-3-(tetrahydropyran-2-yloxy)-estra-1,3,5(10)-triene A solution of 21.3 g of 17β-acetoxy-7α-(5-acetoxypentyl)-estra-1,3,5(10)-trien-3-ol in 213 ml of tetrahydrofuran is allowed to stand with 21.3 ml of 3,4-dihydro-2H-pyran and 1.065 g of p-toluenesulfonic acid for 8 hours at room temperature. The reaction solution is mixed with 3 ml of pyridine, then diluted with diethyl ether, washed with water and dried. The residue that is obtained after the concentration by evaporation is chromatographed on silica gel, and 24.3 g of 17β-acetoxy-7α-(5-acetoxypentyl)-3-(tetrahydropyran-2-yloxy)-estra-1,3,5(10)-triene is obtained as an oil. $[\alpha]_D^{22}$=+31.5° (c=0.535% in chloroform)

f) 17β-Acetoxy-7α-(5-hydroxypentyl)-3-(tetrahydropyran-2-yloxy)-estra-1,3,5(10)-triene A solution of 10.2 g of 17β-acetoxy-7α-(5-acetoxypentyl)-3-(tetrahydropyran-2-yloxy)-estra-1,3,5(10)-triene in 205 ml of methanol is stirred with 33.7 ml of sodium hydroxide solution for 45 minutes at 15° C. Then, it is diluted with diethyl ether, washed with water, dried on sodium sulfate and concentrated by evaporation in a vacuum. 5.6 of 17β-acetoxy-7α-(5-hydroxypentyl)-3-(tetrahydropyran-2-yloxy)-estra-1,3,5(10)-triene is obtained. $[\alpha_D^{22}$=+32.2° (c=0.505% in chloroform)

g) 17β-Acetoxy-3-(tetrahydropyran-2-yloxy)-7α-(5-p-toluenesulfonyloxypentyl)-estra-1,3,5(10)-triene A solution of 5.5 g of 17β-acetoxy-7α-(5-hydroxypentyl)-3-(tetrahydropyran-2-yloxy)-estra-1,3,5(10)-triene in 47 ml of pyridine is allowed to stand with 5.5 g of p-toluenesulfonic anhydride for 45 minutes at room temperature. Then, the reaction solution is cooled in an ice bath, mixed with 4 ml of water and stirred for 45 more minutes. It is then diluted with ethyl acetate, washed with water, dried and concentrated by evaporation. 8.2 g of 17β-acetoxy-3-(tetrahydropyran-2-yloxy)-7α-(5-p-toluenesulfonyloxypentyl)-estra-1,3,5(10)-triene is obtained as an oil.

h) 17β-Acetoxy-7α-(5-methylaminopentyl)-3-(tetrahydropyran-2-yloxy)-estra-1,3,5(10)-triene 6.3 g of methylamine is condensed in a pressure pipe while being cooled with ice in a solution of 8.2 g of 17β-acetoxy-3-(tetrahydropyran-2-yloxy)-7α-(5-p-toluenesulfonyloxypentyl)-estra-1,3,5(10)-triene in 80 ml of tetrahydrofuran. The closed pressure pipe is then heated for 6 hours to 60° C. After cooling, it is evaporated to dryness in a vacuum, and the residue is chromatographed on silica gel. 5.1 g of 17β-acetoxy-7α-(5-methylaminopentyl)-3-(tetrahydropyran-2-yloxy)-estra-1,3,5(10)-triene is obtained as an oil. $[\alpha]_D = +29.7°$ (c=0.535% in chloroform)

i) 17β-Acetoxy-7α-{5-[N-methyl-N-3-(4,4,5,5,5-pentafluoropentyl-thio)-propylamino]-pentyl}-3-(tetrahydropyran-2-yloxy)-estra-1,3,5(10)-triene A solution of 1.64 g of 17β-acetoxy-7α-(5-methylaminopentyl)-3-(tetrahydropyran-2-yloxy)-estra-1,3,5(10)-triene in 25 ml of absolute DMF is stirred with 159 mg of 80% sodium hydride under nitrogen for 2 hours at room temperature. 1.43 g of 3-chloropropyl-4,4,5,5,5-pentafluoropentanesulfide in 7 ml of absolute DMF is then added in drops and then stirred for 22 more hours at 80° C. The reaction solution is then diluted with ethyl acetate, washed with water, dried, concentrated by evaporation, and the residue is chromatographed on silica gel. 820 mg of 17β-acetoxy-7α-{5-[N-methyl-N-3-(4,4,5,5,5-pentafluoropentylthio)-propylamino]-pentyl}-3-(tetrahydropyran-2-yloxy-estra-1,3,5(10)-triene is obtained as an oil.

$[\alpha]_D^{22} = +21.5°$ (c=0.51% in chloroform)

j) 7α-{5-[N-Methyl-N-3-(4,4,5,5,5-pentafluoropentylthio)-propylamino]-pentyl}-3-(tetrahydropyran-2-yloxy)-estra-1,3,5(10)-trien-17β-ol A solution of 790 mg of 17β-acetoxy-7α-{5-[N-methyl-N-3-(4,4,5,5,5-pentafluoro-pentylthio)-propylamino]-pentyl}-3-(tetrahydropyran-2-yloxy)-estra-1,3,5(10)-triene in 8 ml of methanol and 3 ml of THF is stirred with 430 mg of potassium carbonate for 18 hours at room temperature. The reaction solution is diluted with diethyl ether, washed with water, dried and concentrated by evaporation. 750 mg of crude 7α-{5-N-methyl-N-3-(4,4,5,5,5-pentafluoropentylthio)-propylamino]-pentyl}-3-(tetrahydropyran-2-yloxy)-estra-1,3,5(10)-trien-17β-ol is obtained.

k) 7α-{5-[N-Methyl-N-3-(4,4,5,5,5-pentafluoropentylthio)-propylamino]-pentyl}-estra-1,3,5(10)-triene-3,17β-dial A solution of 750 mg of 7α-{5-[N-methyl-N-3-(4,4,5,5,5-pentafluoropentylthio)-propylamino]-pentyl}-3-(tetrahydropyran-2-yloxy)-estra-1,3,5(10)-trien-17β-ol in 28 ml of methanol and 2.8 ml of water is stirred with 350 mg of oxalic acid for 17 hours at room temperature. It is then diluted with ethyl acetate, washed with sodium bicarbonate solution and water, dried and concentrated by evaporation. The residue is chromatographed on silica gel, and 640 mg of 7α-{5-[N-methyl-N-3-(4,4,5,5,5-pentafluoropentylthio)-propylamino]-pentyl}-estra-1,3,5(10)-triene-3,17β-diol is obtained as an oil. $[\alpha]_D^{22} +24.0°$ (c=0.515% in chloroform)

Example 2

17α-Methyl-7α-{5-[N-methyl-N-3-(4,4,5,5,5-pentafluoropentyl-thio)-propylamino]-pentyl}-estra-1,3,5(10)-triene-3,17β-diol a) 7α-{5-[N-Methyl-N-3-(4,4,5,5,5-pentafluoro-pentylthio)-propylamino]-pentyl}-3-(tetrahydropyran-2-yloxy)-estra-1,3,5(10)-trien-17-one A solution of 900 mg of 7α-{5-[N-methyl-N-3-(4,4,5,5,5-pentafluoropentylthio)-propylamino]-pentyl}-3-(tetrahydropyran-2-yloxy)-estra-1,3,5(10)-trien-17β-ol is mixed in 30 ml of toluene and 9.6 ml of cyclohexanone with a solution of 900 mg of aluminum isopropylate in 16 ml of toluene and heated for 30 minutes while being distilled off slowly. The reaction solution is then diluted with ethyl acetate, washed with 20% potassium sodium tartrate solution, dried and concentrated by evaporation. The residue is chromatographed on silica gel with hexane/ethyl acetate. 715 mg of 7α-{5-[N-methyl-N-3-(4,4,5,5,5-pentafluoropentylthio)-propylamino]-pentyl}-3-(tetrahydropyran-2-yloxy)-estra-1,3,5(10)-trien-17-one is obtained as an oil.

b) 3-Hydroxy-7α-{5-[N-methyl-N-3-(4,4,5,5,5-pentafluoropentylthio)-propylamino]-pentyl}-estra-1,3,5(10)-trien-17-one A solution of 710 mg of 7α-{5-[N-methyl-N-3-(4,4,5,5,5-pentafluoropentylthio)-propylamino]-pentyl}-3-(tetrahydropyran-2-yloxy)-estra-1,3,5(10)-trien-17-one is reacted as described under 1k, worked up and chromatographed on silica gel with hexane/ethyl acetate. 650 mg of 3-hydroxy-7α-{5-[N-methyl-N-3-(4,4,5,5,5-pentafluoropentylthio)-propylamino]-pentyl}-estra-1,3,5(10)-trien-17-one is obtained as an oil.

c) 17α-Methyl-7α-{5-[N-methyl-N-3-(4,4,5,5,5-pentafluoropentylthio)-propylamino]-pentyl}-estra-1,3,5(10)-triene-3,17β-diol Dried cerium(III) chloride (1.97 g) is stirred in 20 ml of tetrahydrofuran for 25 minutes at room temperature, mixed with 3 ml of a 3 molar methylmagnesium bromide solution while being cooled with ice, and stirred for 30 minutes while being cooled with ice and for minutes at room temperature. In this reaction mixture, a solution of 600 mg of 3-hydroxy-7α-{5-[N-methyl-N-3-(4,4,5,5,5-pentafluoro-pentylthio)-propylamino)-pentyl}-estra-1,3,5(10)-trien-17-one in 6 ml of tetrahydrofuran is added in drops and stirred for 2 more hours at room temperature. While being cooled with ice, the excess reagent is decomposed with saturated ammonium chloride solution, diluted with ethyl acetate, and washed with saturated ammonium chloride solution and water, dried on sodium sulfate and concentrated by evaporation in a vacuum and chromatographed on silica gel with hexane/ethyl acetate. 350 mg of 17α-methyl-7α-{5-[N-methyl-N-3-(4,4,5,5,5-pentafluoropentylthio)-propylamino]-pentyl}-estra-1,3,5(10)-triene-3,17β-diol is obtained as an oil. $[\alpha]_D^{22} +15°$ (c=0.52% in chloroform)

Example 3

17α-Ethinyl-7α-{5-[N-methyl-N-3-(4,4,5,5,5-pentafluoropentylthio)-propylamino]-pentyl}-estra-1,3,5(10)-triene-3,17β-diol a) 17α-Ethinyl-7α-{5-[N-methyl-N-3-(4,4,5,5,5-pentafluoropentylthio)-propylamino]-pentyl}-3-(tetrahydropyran-2-yloxy)-estra-1,3,5(10)-trien-17β-ol In a solution of 336 mg of potassium-tert-butylate in 30 ml of tetrahydrofuran, dry acetylene is introduced until saturation is achieved while being cooled with ice. In this solution, 410 mg of 7α-{5-[N-methyl-N-3-(4,4,5,5,5-pentafluoropentylthio)-propylamino]-pentyl}-3-(tetrahydropyran-2-yloxy)-estra-1,3,5(10)-trien-17-one in 10 ml of tetrahydrofuran is added in drops and stirred for one hour at ice bath temperature. Then, it is diluted with ethyl acetate, washed with water, dried on sodium sulfate and concentrated by evaporation in a vacuum. 440 mg of crude 17α-ethinyl-7α-{5-[N-methyl-N-3-(4,4,5,5,5-pentafluoropentylthio)-propylamino]-pentyl}-3-(tetrahydropyran-2-yloxy)-estra-1,3,5(10)-trien-17β-ol is obtained.

b) 17α-Ethinyl-7α-{5-[N-methyl-N-3-(4,4,5,5,5-pentafluoropentylthio)-propylamino]-pentyl}-estra-1,3,5(10)-triene-3,17β-diol As described in Example 1k, 440 mg of crude 17α-ethinyl-7α-{5-[N-methyl-N-3-(4,4,5,5,5-pentafluoropentylthio)-propylamino]-pentyl}-3-(tetrahydropyran-2-yloxy)-estra-1,3,5(10)-trien-17β-ol is reacted, worked up and chromatographed on silica gel with hexane/ethyl acetate. 275 mg of 17α-ethinyl-7α-{5-[N-methyl-N-3-(4,4,5,5,5-pentafluoropentylthio)-propylamino]-pentyl}-estra-1,3,5(10)-triene-3,17β-diol is obtained as an oil.

$[\alpha]_D^{22}$=+3.2° (c=0.52% in chloroform)

Example 4

7α-{5-[N-Methyl-N-2-(4,4,5,5,5-pentafluoropentanesulfonyl)-ethylamino]-pentyl}-ostra-1,3,5(10)-triene-3,17β-diol a) 7α-{5-Methylaminopentyl}-3-(tetrahydropyran-2-yloxy)-estra-1,3,5(10)-trien-17β-ol A solution of 307 mg of 17β-acetoxy-7α-{5-methylaminopentyl}-3-(tetrahydropyran-2-yloxy)-estra-1,3,5(10)-triene (Example 1h) in 6 ml of methanol is stirred with 1.5 ml of sodium hydroxide solution for 4 hours at room temperature. Then, it is diluted with ethyl acetate, washed with water, dried on sodium sulfate and concentrated by evaporation in a vacuum. 285 mg of 7α-{5-methylaminopentyl}-3-(tetrahydropyran-2-yloxy)-estra-1,3,5(10)-trien-17β-ol is obtained.

b) 7α-{5-[N-Methyl-N-2-(4,4,5,5,5-pentafluoropentanesulfonyl)-ethylamino]-pentyl}-3-(tetrahydropyran-2-yloxy)-estra-1,3,5(10)-trien-17β-ol A solution of 270 mg of 7α-{5-methylaminopentyl}-3-(tetrahydropyran-2-yloxy)-estra-1,3,5(10)-trien-17β-ol in 9.5 ml of methanol is stirred with 250 mg of vinyl-4,4,5,5,5-pentafluoropentanesulfonane sulfone for 23 hours at 60° C. Then, it is diluted with ethyl acetate, washed with water, dried on sodium sulfate, concentrated by evaporation in a vacuum and chromatographed on silica gel with hexane/ethyl acetate. 285 mg of 7α-{5-[N-methyl-N-2-(4,4,5,5,5-pentafluoropentanesulfonyl)-ethylamino]-pentyl}-3-(tetrahydropyran-2-yloxy)-estra-1,3,5(10)-trien-17β-ol is obtained as an oil.

c) 7α-{5-[N-Methyl-N-2-(4,4,5,5,5-pentafluoropentanesulfonyl)-ethylamino]-pentyl}-estra-1,3,5(10)-triene-3,17β-diol A solution of 275 mg of 7α-{5-[N-methyl-N-2-(4,4,5,5,5-pentafluoropentanesulfonyl)-ethylamino]-pentyl}-3-(tetrahydropyran-2-yloxy)-estra-1,3,5(10)-trien-17β-ol is reacted as described in Example 1k, worked up and chromatographed on silica gel with hexane/ethyl acetate. 250 mg of 7α-{5-[N-methyl-N-2-(4,4,5,5,5-pentafluoropentanesulfonyl)-ethylamino]-pentyl}-estra-1,3,5(10)-triene-3,17β-diol is obtained.

$[\alpha]_D^{22}$+23.6° (c=0.52% in chloroform)

Example 5

7α-{5-[N-Methyl-N-3-(4,4,5,5,5-pentafluoropentanesulfonyl)-propylamino]-pentyl}-estra-1,3,5(10)-triene-3,17β-diol a) 17β-Acetoxy-7α-{5-[N-methyl-N-3-(4,4,5,5,5-pentafluoropentanesulfonyl)-propylamino]-pentyl}-3-(tetrahydropyran-2-yloxy)-estra-1,3,5(10)-triene A solution of 400 mg of 17β-acetoxy-7α-{5-methylaminopentyl}-3-(tetrahydropyran-2-yloxy)-estra-1,3,5(10)-triene (Example 1h) is reacted with 485 mg of 3-chloropropyl-4,4,5,5,5-pentafluoro-pentanesulfone as described in Example 1i, worked up and chromatographed on silica gel with hexane/ethyl acetate. 190 mg of 17β-acetoxy-7α-{5-[N-methyl-N-3-(4,4,5,5,5-pentafluoropentanesulfonyl)-propylamino]-pentyl}-3-(tetrahydropyran-2-yloxy)-estra-1,3,5(10)-triene is obtained as an oil.

b) 7α-{5-[N-Methyl-N-3-(4,4,5,5,5-pentafluoropentanesulfonyl)-propylamino]-pentyl}-3-(tetrahydropyran-2-yloxy)-estra-1,3,5(10)-trien-3-ol A solution of 190 mg of 17β-acetoxy-7α-{5-[N-methyl-N-3-(4,4,5,5,5-pentafluoropentanesulfonyl)-propylamino]-pentyl}-3-(tetrahydropyran-2-yloxy)-estra-1,3,5(10)-triene is reacted as described in Example 1k, worked up and chromatographed on silica gel with hexane/ethyl acetate. 95 mg of 17β-acetoxy-7α-{5-[N-methyl-N-3-(4,4,5,5,5-pentafluoropentanesulfonyl)-propylamino]-pentyl}-estra-1,3,5(10)-trien-3-ol is obtained as an oil.

c) 7α-{5-[N-Methyl-N-3-(4,4,5,5,5-pentafluoropentanesulfonyl)-propylamino]-pentyl}-estra-1,3,5(10)-triene-3,17β-diol A solution of 95 mg of 17β-acetoxy-7α-{5-[N-methyl-N-3-(4,4,5,5,5-pentafluoropentanesulfonyl)-propylamino]-pentyl}-estra-1,3,5(10)-trien-3-ol is reacted as described in Example 1i, worked up and chromatographed on silica gel with hexane/ethyl acetate. 55 mg of 7α-{5-[N-methyl-N-3-(4,4,5,5,5-pentafluoropentanesulfonyl)-propylamino]-pentyl}-estra-1,3,5(10)-triene-3,17β-diol is obtained.

Example 6

7α-{5-[N-Methyl-N-3-(4,4,5,5,5-pentafluoropentanesulfinyl)-propylamino]-pentyl}-estra-1,3,5(10)-triene-3,17β-diol A solution of 200 mg of 7α-{5-[N-methyl-N-3-(4,4,5,5,5-pentafluoropentylthio)-propylamino]-pentyl}-estra-1,3,5(10)-triene-3,17β-diol in 8.1 ml of methanol and 1.7 ml of water is stirred with 101 mg of sodium periodate for 2 hours at room temperature. It is diluted with ethyl acetate, washed with water, dried and concentrated by evaporation. The residue is chromatographed on silica gel, and 150 mg of 7α-{5-[N-methyl-N-3-(4,4,5,5,5-pentafluoropentanesulfinyl)-propylamino]-pentyl}-estra-1,3,5(10)-triene-3,17β-diol is obtained as an oil.

Example 7

7α-{5-[N-Methyl-N-4-(4,4,5,5,5-pentafluoropentylthio)-butylamino]-pentyl}-estra-1,3,5(10)-triene-3,17β-diol a) 17β-Acetoxy-7α-{5-[N-methyl-N-4-(4,4,5,5,5-pentafluoropentylthio)-3-(tetrahydropyran-2-yloxy)-butylamino]-pentyl}-estra-1,3,5(10)-triene A solution of 835 mg of 17β-acetoxy-7α-(5-methylaminopentyl)-3-(tetrahydropyran-2-yloxy)-estra-1,3,5(10)-triene (Example 1h) is reacted with 969 mg of 4-chlorobutyl-4,4,5,5,5-pentafluoropentylsulfide as described in Example 1i, worked up and chromatographed on silica gel with hexane/ethyl acetate. 675 mg of 17β-acetoxy-7α-{5-[N-methyl-N-4-(4,4,5,5,5-pentafluoropentylthio)-3-(tetrahydropyran-2-yloxy)-butylamino]-pentyl}-estra-1,3,5(10)-triene is obtained as an oil.

b) 7α-{5-[N-Methyl-N-4-(4,4,5,5,5-pentylfluoropentylthio)-3-(tetrahydropyran-2-yloxy)-butylamino]-pentyl}-estra-1,3,5(10)-trien-3-ol A solution of 660 mg of 17β-acetoxy-7α-{5-[N-methyl-N-4-(4,4,5,5,5-pentafluoropentylthio)-3-(tetrahydropyran-2-yloxy)-butylamino]-pentyl}-estra-1,3,5(10)-triene is reacted as described in Example 1j, worked up and chromatographed on silica gel with dichloromethane/methanol. 530 mg of 7α-{5-(N-methyl-N-4-(4,4,5,5,5-pentafluoropentylthio)-3-(tetrahydropyran-2-yloxy)-butylamino]-pentyl}-estra-1,3,5(10)-trien-3-ol is obtained as an oil.

c) 7α-{5-[N-Methyl-N-4-(4,4,5,5,5-pentafluoropentylthio)-butylamino]-pentyl}-estra-1,3,5(10)-trione-3,17β-diol A solution of 530 mg of 7α-{5-[N-methyl-N-4-(4,4,5,5,5-pentafluoropentylthio)-3-(tetrahydropyran-2-yloxy)-butylamino]-pentyl}-estra-1,3,5(10)-trien-3-ol is reacted as described in Example 1k, worked up and chromatographed on silica gel with dichloromethane/methanol. 470 mg of 7α-{5-[N-methyl-N-4-(4,4,5,5,5-pentafluoropentylthio)-butylamino]-pentyl}-estra-1,3,5(10)-triene-3,17β-diol is obtained as an oil. $[\alpha]_D^{22}=+20.5°$ (c=0.515% in chloroform).

Example 8

2-Fluoro-7α-{5-[N-methyl-N-3-(4,4,5,5,5-pentafluoropentylthio)-propylamino]-pentyl}-estra-1,3,5(10)-triene-3,17β-diol a) 7α-(5-tert-Butyl-dimethylsilyloxypentyl)-estr-4-ene-3,17-dione In 70 ml of absolute tetrahydrofuran, 15.1 g of Mg chips with 175.6 g of 1-bromo-5-tert-butyl-dimethylsilyloxypentane [Tetrahedron Letters 23, 1982, 40, 4147–4150], dissolved in 600 ml of absolute tetrahydrofuran, are reacted to form the Grignard reagent. 59 g of copper(I) iodide is added to this solution, cooled to –20° C., under a nitrogen stream, and then 50 g of estra-4,6-diene-3,17-dione [Steroids Vol. 1, 1963, 233–249], dissolved in 300 ml of absolute THF, is added in drops within one hour. For working-up, 37.5 ml of acetic acid is added in drops, the reaction mixture is diluted with ethyl acetate, washed with saturated ammonium chloride solution, water and sodium bicarbonate solution and dried. The residue that is obtained after the concentration by evaporation is chromatographed on silica gel. 35.4 g of 7α-(5-tert-butyldimethylsilyloxypentyl)-estr-4-ene-3,17-dione is obtained. $[\alpha]_D^{22}=+52.8°$ (c=0.535% in chloroform)

b) 7α-(5-Hydroxypentyl)-estr-4-ene-3,17-dione

A solution of 125.4 g of 7α-(5-tert-butyldimethylsilyloxypentyl)-estr-4-ene-3,17-dione in 625 ml of methanol and 347 ml of water is stirred with 694 ml of glacial acetic acid for 2.5 hours at 50° C. After the concentration by evaporation at 60° C. in a vacuum, 94.1 g of crude 7α-(5-hydroxypentyl)-estr-4-ene-3,17-dione is obtained as an oil.

c) 7α-(5-Acetoxypentyl)-estr-4-ene-3,17-dione

A solution of 94 g of crude 7α-(5-hydroxypentyl)-estr-4-ene-3,17-dione in 620 ml of pyridine is slowly mixed with 310 ml of acetic anhydride and stirred for 2 hours at 25° C. Then, it is slowly mixed with 116 ml of water while being cooled with ice, diluted with 3 l of diethyl ether, the organic phase is dried and concentrated by evaporation after washing with sodium bicarbonate solution. The residue is chromatographed on silica gel, and 84.4 g of 7α-(5-acetoxypentyl)-estr-4-ene-3,17-dione is obtained as an oil.

d) 7α-(5-Acetoxypentyl)-3-hydroxy-estra-1,3,5(10)-trien-17-one 17.8 g of lithium bromide and 92.83 g of copper(II) bromide are added to a solution of 82.3 g of 7α-(5-acetoxypentyl)-estr-4-ene-3,17-dione in 936 ml of acetonitrile at a bath temperature of 80° C. After 10 minutes at a bath temperature of 80° C., the reaction solution is cooled, mixed with water, extracted three times with ethyl acetate, the organic phase is washed with water and sodium bicarbonate solution and dried. The residue that is obtained after the concentration by evaporation is chromatographed on silica gel, and 60.4 g of 7α-(5-acetoxypentyl)-3-hydroxy-estra-1,3,5(10)-trien-17-one is obtained as an oil.

e) 7α-(5-Acetoxypentyl)-estra-1,3,5(10)-triene-3,17β-diol 6.0 g of 7α-(5-acetoxypentyl)-3-hydroxy-estra-1,3,5(10)-trien-17-one is dissolved in 65 ml of tetrahydrofuran, and 2 ml of water and 0.6 g of fine sodium borohydride are added at room temperature. After 1 hour of stirring at room temperature, the reaction mixture is added to ice water, extracted three times with ethyl acetate, and the organic phase is washed with sodium chloride solution, dried with sodium sulfate and concentrated by evaporation in a vacuum, raw yield 6.07 g.

f) 7α-(5-Acetoxypentyl)-3,17β-bis-(tetrahydropyran-2-yloxy)-estra-1,3,5(10)-triene 5.6 g of crude 7α-(5-acetoxypentyl)-estra-1,3,5(10)-triene-3,17β-diol is dissolved in 35 ml of anhydrous tetrahydrofuran and mixed with 3.5 ml of dihydropyran and 0.18 g of p-toluenesulfonic acid. The mixture is stirred at room temperature overnight, then diluted with ethyl acetate, and the mixture is shaken out in succession with saturated sodium bicarbonate solution and saturated common salt solution. The organic phase is dried with sodium sulfate and concentrated by evaporation in a vacuum, yield 8.31 g.

g) 7α-(5-Benzenesulfonyloxypentyl)-3,17β-bis-(tetrahydropyran-2-yloxy)-2-fluoroestra-1,3,5(10)-triene and 7α-(5-benzenesulfonyloxypentyl)-17β-(tetrahydropyran-2-yloxy)-2-fluoro-estra-1,3,5(10)-trien-3-ol 8.8 g of 7α-(5-acetoxypentyl)-3,17β-bis-(tetrahydropyran-2-yloxy)-estra-1,3,5(10)-triene, not further purified, is dissolved in 220 ml of anhydrous tetrahydrofuran. In an inert gas atmosphere, it is cooled to –70° C. and mixed with 88 ml of an approximately 1.3 molar solution of sec-butyllithium in hexane. It is then stirred for 30 minutes at –70° C. and for 30 minutes at 0° C., cooled again to –70° C., and the solution of 34.68 g of N-fluorobenzenesulfonimide in 280 ml of anhydrous tetrahydrofuran is added in drops. It is again stirred for 30 minutes at –70° C. and for 30 minutes at 0° C., then poured into a saturated sodium bicarbonate solution and extracted three times with ethyl acetate. The combined organic phases are shaken out with saturated common salt solution, dried with sodium sulfate and concentrated by evaporation in a vacuum. The raw yield of 26 g is chromatographed twice on silica gel with hexane, whereby 1.52 g of 7α-(5-benzenesulfonyloxypentyl)-3,17β-bis-(tetrahydropyran-2-yloxy)-2-fluoro-estra-1,3,5(10)-triene is obtained as an oil and 210 mg of 7α-(5-benzenesulfonyloxypentyl)-17β-(tetrahydropyran-2-yloxy)-2-fluoro-estra-1,3,5(10)-trien-3-ol is obtained as an oil.

h) 2-Fluoro-7α-[5-[N-methyl-N-3-(4,4,5,5,5-pentafluoropentylthio)-propylamino]-pentyl}-17β-(tetrahydropyran-2-yloxy)-estra-1,3,5(10)-trien-3-ol 130 mg of methyl-[3-(4,4,5,5,5-pentafluoropentylthio)-propyl]-amine is added to a solution of 210 mg of the above-obtained 7α-(5-benzenesulfonyloxypentyl)-17β-(tetrahydropyran-2-yloxy)-2-fluoro-estra-1,3,5(10)-trien-3-ol in 1.8 ml of anhydrous dimethylformamide, and it is heated in an inert gas atmosphere for 6 hours to 100° C. After cooling, it is diluted again with ethyl acetate, mixed with sodium bicarbonate solution, and the aqueous phase is shaken out twice with ethyl acetate, the combined organic phases are shaken out with saturated common salt solution, and the organic phase is dried with sodium sulfate and liberated of solvent in a vacuum. The residue of 292 mg is chromatographed on silica gel with ethyl acetate and methanol, and 105 mg of 2-fluoro-7α-{5-[N-methyl-N-3-(4,4,5,5,5-pentafluoropentylthio)-propylamino]-pentyl}-17β-(tetrahydropyran-2-ylxoy)-estra-1,3,5(10)-trien-3-ol is obtained as an oil.

i) 2-Fluoro-7α-{5-[N-methyl-N-3-(4,4,5,5,5-pentafluoropentylthio)-propylamino]-pentyl}-estra-1,3,5,(10)-trione-3, 17β-diol The 105 mg of 2-fluoro-7α-{5-[N-methyl-N-3-(4,4,5,5,5-pentafluoropentylthio)-propylamino]-pentyl}-17β-tetrahydropyran-2-yloxy)-estra-1,3,5(10)-trien-3-ol and 60 mg of oxalic acid that are obtained are dissolved in 3 ml of methanol and 0.3 ml of water, heated for 45 minutes to 60° C., mixed after cooling with ethyl acetate, and dispersed as described above between saturated sodium bicarbonate solution and ethyl acetate. The organic phase is washed with sodium chloride solution, dried in sodium sulfate and concentrated by evaporation in a vacuum. By preparative thin-layer chromatography on silica gel with ethyl acetate/methanol 9:1 as a mobile solvent, 46 mg of 2-fluoro-7α-{5-[N-methyl-N-3-(4,4,5,5,5-pentafluoropentylthio)-propylamino]-pentyl]-estra-1,3,5(10)-triene-3,17β-diol is obtained as an oil with a rotation of $[\alpha]_D^{22}$=+24.0° (c=0.1% in chloroform).

Example 9

2-Fluoro-17α-methyl-7α-{5-[N-methyl-N-3-(4,4,5,5,5-pentafluoropentylthio)-propylamino]-pentyl}-estra-1,3,5(10)-triene-3,17β-diol a) 2-Fluoro-7α-{5-[N-methyl-N-3-(4,4,5,5,5-pentafluoropentylthio)-propylamino]-pentyl}-estra-1,3,5(10)-trien-3-ol-17-one 70 mg of 2-fluoro-7α-{5-[N-methyl-3-(4,4,5,5,5-pentafluoropentylthio)-propylamino]-pentyl}-estra-1,3,5(10)-trien-3-ol-17-one, as described in Example 2a), is obtained as an oil from 83 mg of 2-fluoro-7α-{5-[N-methyl-N-3-(4,4,5,5,5-pentafluoropentylthio)-propylamino]-pentyl}-estra-1,3,5(10)-triene-3,17β-diol.

b) 2-Fluoro-17α-methyl-7α-{5-[N-methyl-N-3-(4,4,5,5,5-pentafluoropentylthio)-propylamino]-pentyl}-estra-1,3,5(10)-triene-3,17β-diol As described in Example 2c), 32 mg of 2-fluoro-17α-methyl-7α-{5-[N-methyl-N-3-(4,4,5,5,5-pentafluoropentylthio)-propylamino]-pentyl}-estra-1,3,5 (10)-triene-3,17β-diol is obtained as an oil from 65 mg of 2-fluoro-7α-{5-[N-methyl-N-3-(4,4,5,5,5-pentafluoropentylthio)-propylamino]-pentyl}-estra-1,3,5 (10)-trien-3-ol-17-one.

Example 10

2-Fluoro-7α-{5-[N-methyl-3-(4,4,5,5,5-pentafluoropentanesulfinyl)-propylamino]-pentyl}-estra-1,3,5(10)-triene-3,17β-diol As in Example 1, 44 mg of 2-fluoro-7α-{5-[N-methyl-3-(4,4,5,5,5-pentafluoropentanesulfinyl)-propylamino]-pentyl}-estra-1,3,5(10)-triene-3,17β-diol is obtained as a solid foam by oxidation with sodium periodate from 75 mg of 2-fluoro-7α-{5-[N-methyl-N-3-(4,4,5,5,5-pentafluoropentylthio)-propylamino]-pentyl}-estra-1,3,5 (10)-triene-3,17β-diol.

Example 11

2-Fluoro-17α-methyl-7α-{5-[N-methyl-N-3-(4,4,5,5,5-pentafluoropentanesulfonyl)-propylamino]-pentyl}-estra-1,3,5(10)-triene-3,17β-diol a) 3,17β-Bis-(tetrahydropyran-2-yloxy)-2-fluoro-7α-{5-[N-methyl-N-3-(4,4,5,5,5-pentafluoropentanesulfonyl)-propylamino]-pentyl}-estra-1,3,5(10)-triene 283 mg of 7α-{5-benzenesulfonyloxypentyl)-3,17β-bis-(tetrahydropyran-2-yloxy)-2-fluoro-estra-1,3,5(10)-triene from Example 6g), as described in Example 6h), is reacted with 250 mg of methyl-[3-(4,4,5,5,5-pentafluoropentanesulfonyl)-propyl]-amine, and 180 mg of 3,17β-bis-(tetrahydropyran-2-yloxy)-2-fluoro-7α-{5-[N-methyl-N-3-(4,4,5,5,5-pentafluoropentane-sulfonyl)-propylamino]-pentyl}-estra-1,3,5(10)-triene is obtained as an oil.

b) 2-Fluoro-7α-{5-[N-methyl-N-3-(4,4,5,5,5-pentafluoropentanesulfonyl)-propylamino]-pentyl}-estra-1,3,5(10)-triene-3,17β-diol For cleavage of THP-ethers with oxalic acid, 180 mg of 3,17β-bis-(tetrahydropyran-2-yloxy)-2-fluoro-7α-{5-[N-methyl-N-3-(4,4,5,5,5-pentafluoropentanesulfonyl)-propylamino]-pentyl}-estra-1,3,5(10)-triene is dissolved in methanol and water, and 123 mg of 2-fluoro-7α-{5-[N-methyl-N-3-(4,4,5,5,5-pentafluoropentanesulfonyl)-propylamino]-pentyl}-estra-1,3,5(10)-triene-3,17β-diol is obtained as a solid foam as described in Example 6i).

c) 2-Fluoro-7α-{5-[N-Methyl-N-3-(4,4,5,5,5-pentafluoropentanesulfonyl)-propylamino]-pentyl}-estra-1,3,5(10)-trien-3-ol-17-one As described in Example 2a), 70 mg of 2-fluoro-7α-{5-[N-methyl-N-3-(4,4,5,5,5-pentafluoropentanesulfonyl)-propylamino]-pentyl}-estra-1,3,5(10)-triene-3,17β-diol is oxidized, whereby 52 mg of 2-fluoro-7α-{5-[N-methyl-N-3-(4,4,5,5,5-pentafluoropentanesulfonyl)-propylamino]-pentyl}-estra-1,3,5(10)-trien-3-ol-17-one is obtained.

d) 2-Fluoro-17α-methyl-7α-{5-[N-methyl-N-3-(4,4,5,5,5-pentafluoropentanesulfonyl)-propylamino]-pentyl}-estra-1,3,5(10)-triene-3,17β-diol As described in Example 2c), 38 mg of 2-fluoro-17α-methyl-7α-{5-[N-methyl-N-3-(4,4,5,5,5-pentafluoropentanesulfonyl)-propylamino]-pentyl}-estra-1,3,5(10)-triene-3,17β-diol is obtained as a solid foam from 45 mg of 2-fluoro-7α-{5-[N-methyl-N-3-(4,4,5,5,5-pentafluoropentanesulfonyl)-propylamino]-pentyl}-estra-1,3,5(10)-trien-3-ol-17-one by Grignard reaction.

Example 12

7α-{5-[N-Methyl-N-4-(4,4,5,5,5-pentafluoropentanesulfinyl)-butylamino]-pentyl}-estra-1,3,5(10)-triene-3,17β-diol A solution of 150 mg of 7α-{5-[N-methyl-N-4-(4,4,5,5,5-pentafluoropentylthio)-butylamino]-pentyl}-estra-1,3,5(10)-triene-3,17β-diol is reacted as described in Example 6, worked up and chromatographed on silica gel with dichloromethane/methanol. 140 mg of 7α-{5-[N-methyl-N-4-(4,4,5,5,5-pentafluoropentanesulfinyl)-butylamino]-pentyl}-estra-1,3,5(10)-triene-3,17β-diol is obtained as a solid foam. $[\alpha]_D^{22}=+22.9°$ (c=0.505% in methanol).

Example 13

17α-Methyl-7α-{5-[N-methyl-N-3-(4,4,5,5,5-pentafluoropentanesulfinyl)-propylamino]-pentyl}-estra-1,3,5(10)-triene-3,17β-diol A solution of 390 mg of 17α-methyl-7α-{5-[N-methyl-N-3-(4,4,5,5,5-pentafluoropentylthio)-propylamino]-pentyl}-estra-1,3,5(10)-triene-3,17β-diol is reacted as described in Example 6, worked up and chromatographed on silica gel with dichloromethane/methanol. 260 mg of 17α-methyl-7α-{5-[N-methyl-N-3-(4,4,5,5,5-pentafluoropentanesulfinyl)-propylamino]-pentyl}-estra-1,3,5(10)-triene-3,17b-diol is obtained as a foam. $[\alpha]_D^{22}=+1.3°$ (c=0.51% in chloroform).

Example 14

17α-Methyl-7α-{5-[N-methyl-N-3-(4,4,5,5,5-pentafluoropentanesulfonyl)-propylamino]-pentyl}-estra-1,3,5(10)-triene-3,17β-diol a) 7α-{5-tert-Butyl-dimethylsilyloxypentyl)-estr-4-ene-3,17-dione In 70 ml of absolute tetrahydrofuran, 15.1 g of Mg chips with 175.6 g of 1-bromo-5-tert-butyl-dimethylsilyloxypentane [Tetrahedron Letters 23, 1982, 40, 4147–4150], dissolved in 600 ml of absolute tetrahydrofuran, are reacted to form the Grignard reagent. 59 g of copper(I) iodide is added to this solution, cooled to −20° C., under a nitrogen stream, and then 50 g of estra-4,6-diene-3,17-dione [Steroids Vol. 1, 1963, 233–249], dissolved in 300 ml of absolute THF, is added in drops within one hour. For working-up, 37.5 ml of acetic acid is added in drops, the reaction mixture is diluted with ethyl acetate, washed with saturated ammonium chloride solution, water and sodium bicarbonate solution and dried. The residue that is obtained after the concentration by evaporation is chromatographed on silica gel. 35.4 g of 7α-(5-tert-butyl-dimethylsilyloxypentyl)-estr-4-ene-3,17-dione is obtained. $[\alpha]_D^{22}=+52.8°$ (c=0.535% in chloroform)

b) 7α-(5-Hydroxypentyl)-estr-4-ene-3,17-dione

A solution of 125.4 g of 7α-(5-tert-butyl-dimethylsilyloxypentyl)-estr-4-ene-3,17-dione in 625 ml of methanol and 347 ml of water is stirred with 694 ml of glacial acetic acid for 2.5 hours at 50° C. After concentration by evaporation at 60° C. in a vacuum, 94.1 g of crude 7α-(5-hydroxypentyl)-estr-4-ene-3,17-dione is obtained as an oil.

c) 17β-Acetoxy-7α-(5-acetoxypentyl)-estr-4-ene-3,17-dione

A solution of 94 g of crude 7α-(5-hydroxypentyl)-estr-4-ene-3,17-dione in 620 ml of pyridine is slowly mixed with 310 ml of acetic anhydride and stirred for 2 hours at 25° C. Then, it is slowly mixed with 116 ml of water while being cooled with ice, diluted with 3 l of diethyl ether, and, after washing with sodium bicarbonate solution, the organic phase is dried and concentrated by evaporation. The residue is chromatographed on silica gel, and 84.4 g of 7α-(5-acetoxypentyl)-estr-4-ene-3,17-dione is obtained as an oil.

d) 7α-(5-Acetoxypentyl)-3-hydroxy-estra-1,3,5(10)-trien-17-one 17.8 g of lithium bromide and 92.83 g of copper(II) bromide are added to a solution of 82.3 g of 7α-(5-acetoxypentyl)-estr-4-ene-3,17-dione in 936 ml of acetonitrile at a bath temperature of 80° C. After 10 minutes at a bath temperature of 80° C., the reaction solution is cooled, extracted three times with ethyl acetate, washed with water and sodium bicarbonate solution and dried. The residue that is obtained after the concentration by evaporation is chromatographed on silica gel, and 60.4 g of 7α-(5-acetoxypentyl)-3-hydroxy-estra-1,3,5(10)-trien-17-one is obtained as an oil.

e) 7α-(5-Acetoxypentyl)-3-(tetrahydropyran-2-yloxy)-estra-1,3,5(10)-trien-17-one A solution of 25.1 g of 7α-(5-acetoxypentyl)-3-hydroxy-estra-1,3,5(10)-trien-17-one is reacted as described in Example 1e, worked up and chromatographed on silica gel with hexane/ethyl acetate. 28.3 g of 7α-(5-acetoxypentyl) 3-(tetrahydropyran-2-yloxy)-estra-1,3,5(10)-trien-17-one is obtained as an oil.

f) 3-(Tetrahydropyran-2-yloxy)-7α-(5-p-tosyloxypentyl)-estra-1,3,5(10)-trien-17-one A solution of 19.7 g of 7α-(5-acetoxypentyl)-3-(tetrahydropyran-2-yloxy)-estra-1,3,5(10)-trien-17-one is saponified as described in Example 1f and tosylated according to Example 1g and worked up. 14.5 g of 3-(tetrahydropyran-2-yloxy)-7α-(5-p-tosyloxypentyl)-estra-1,3,5(10)-trien-17-one is obtained as an oil.

g) 7α-{5-[N-Methyl-N-3-(4,4,5,5,5-pentafluoropentanesulfonyl)-propylamino]-pentyl}-3-(tetrahydropyran-2-yloxy)-estra-1,3,5(10)-trien-17-one A solution of 1.5 g of 3-(tetrahydropyran-2-yloxy)-7α-(5-tosyloxypentyl)-estra-1,3,5(10)-trien-17-one in 21 ml of ethyl methyl ketone is stirred with 716 mg of potassium carbonate, 171 mg of potassium iodide and 1.5 g of methyl-[3-(4,4,5,5,5-pentafluoropentanesulfonyl)-propyl]-amine for 4 hours at 80° C. under nitrogen. Then, it is diluted with ethyl acetate, washed with water, dried on sodium sulfate, concentrated by evaporation in a vacuum and chromatographed on silica gel with dichloromethane/methanol. 1.39 g of 7α-{5-[N-methyl-N-3-(4,4,5,5,5-pentafluoro-pentanesulfonyl)-propylamino]-pentyl}-3-(tetrahydropyran-2-yloxy)-estra-1,3,5(10)-trien-17-one is obtained as an oil.

h) 17α-Methyl-7α-{5-[N-methyl-N-3-(4,4,5,5,5-pentafluoropentanesulfonyl)-propylamino]-pentyl}-3-(tetrahydropyran-2-yloxy)-estra-1,3,5(10)-trien-17β-ol As described in Example 2c, 690 mg of 7α-{5-[N-methyl-N-3-(4,4,5,5,5-pentafluoro-pentanesulfonyl)-propylamino]-pentyl}-3-(tetrahydropyran-2-yloxy)-estra-1,3,5(10)-trien-17-one is reacted, worked up and chromatographed on silica gel with dichloromethane/methanol. 460 mg of 17α-methyl-7α-{5-[N-methyl-N-3-(4,4,5,5,5-pentafluoropentanesulfonyl)-propylamino]-pentyl}-3-(tetrahydropyran-2-yloxy)-estra-1,3,5(10)-trien-17β-ol is obtained.

i) 17α-Methyl-7α-{5-[N-methyl-N-3-(4,4,5,5,5-pentafluoropentanesulfonyl)-propylamino]-pentyl}-estra-1,3,5(10)-triene-3,17β-diol A solution of 460 mg of 17α-methyl-7α-{5-[N-methyl-N-3-(4,4,5,5,5-pentafluoro-pentanesulfonyl)-propylamino]-pentyl}-3-(tetrahydropyran-2-yloxy)-estra-1,3,5(10)-triene-17β-ol is reacted as described in Example 1k, worked up and chromatographed on silica gel with dichloromethane/methanol. 380 mg of 17α-methyl-7α-{5-[N-methyl-N-3-(4,4,5,5,5-pentafluoropentane-sulfonyl)-propylamino]-pentyl}-estra-1,3,5(10)-triene-3,17β-diol is obtained as a solid foam. $[\alpha]_D^{22}$=+12.3° (c=0.525% in chloroform).

Example 15

17α-Ethinyl-7α-{5-[N-methyl-N-3-(4,4,5,5,5-pentafluoropentanesulfonyl)-propylamino]-pentyl}-estra-1,3,5(10)-triene-3,17β-diol a) 17α-Ethinyl-7α-{5-[N-methyl-N-3-(4,4,5,5,5-pentafluoropentanesulfonyl)-propylamino]-pentyl}-3-(tetrahydropyran-2-yloxy)-estra-1,3,5(10)-trien-17-ol 8.3 ml of a 3 molar ethylmagnesium bromide solution is added in drops to 9 ml of an ice-cooled tetrahydrofuran-acetylene solution. Then, a solution of 660 mg of 7α-{5-[N-methyl-N-3-(4,4,5,5,5-pentafluoropentanesulfonyl)-propylamino]-pentyl}-3-(tetrahydropyran-2-yloxy)-estra-1,3,5(10)-trien-17-one in 5 ml of tetrahydrofuran is added in drops, and it is stirred for 2 hours at room temperature. The reaction solution is diluted with ethyl acetate, washed with saturated ammonium chloride solution and water, dried on sodium sulfate, concentrated by evaporation in a vacuum and chromatographed on silica gel with dichloromethane/methanol. 550 mg of 17α-ethinyl-7α-{5-[N-methyl-N-3-(4,4,5,5,5-pentafluoropentanesulfonyl)-propylamino]-pentyl}-3-(tetrahydropyran-2-yloxy)-estra-1,3,5(10)-trien-17-ol is obtained as an oil.

b) 17α-Ethinyl-7α-{5-[N-methyl-N-3-(4,4,5,5,5-pentafluoropentanesulfonyl)-propylamino]-pentyl}-estra-1,3,5(10)-triene-3,17β-diol A solution of 540 mg of 17α-ethinyl-7α-{5-[N-methyl-N-3-(4,4,5,5,5-pentafluoropentanesulfonyl)-propylamino]-pentyl}-3-(tetrahydropyran-2-yloxy)-estra-1,3,5(10)-trien-17-ol is reacted as described in Example 1k, worked up and chromatographed on silica gel with dichloromethane/methanol. 420 mg of 17α-ethinyl-7α-{5-[N-methyl-N-3-(4,4,5,5,5-pentafluoropentanesulfonyl)-propylamino]-pentyl}-estra-1,3,5(10)-triene-3,17β-diol is obtained as a solid foam. $[\alpha]_D^{22}$=+0.9° (c=0.51% in chloroform)

Synthesis of the Starting Compounds

3-Chloropropyl-4,4,5,5,5-pentafluoropentyl sulfide 7.08 g of 4,4,5,5,5-pentafluoropentyl-1-thioacetate is added in drops to a mixture of 6 ml of methanol and 6 ml of 30% methanolic sodium methylate solution at ice bath temperature, and it is stirred for 30 more minutes at room temperature. This solution is then dissolved at room temperature to 12.2 g of 1-chloro-3-iodopropane in 12 ml of methanol, added in drops, and stirred for 3 more hours. It is then diluted with diethyl ether, washed with water and dried. After concentration by evaporation, the residue is chromatographed on silica gel, and 7.5 g of 3-chloropropyl-4,4,5,5,5-pentafluoropentyl sulfide is obtained. A distilled sample has a boiling point of 95–100° C. at 15 Torr.

4-Chlorobutyl-4,4,5,5,5-pentafluoropentyl sulfide

Analogously to what is described for 3-chloropropyl-4,4,5,5,5-pentafluoropentyl sulfide, 4-chlorobutyl-4,4,5,5,5-pentafluoropentyl sulfide is obtained if 1-chloro-3-iodopropane is replaced by 1-chloro-4-iodobutane.

Vinyl-4,4,5,5,5-pentafluoropentylsulfone a) Vinyl-4,4,5,5,5-pentafluoropentyl sulfide 2.36 g of 4,4,5,5,5-pentafluoropentyl-1-thioacetate is added in drops to a mixture of 2.5 ml of methanol and 2 ml of 30% methanolic sodium methanolate solution at ice bath temperature, and it is stirred for 30 minutes at room temperature. This solution is added in drops at room temperature to a solution of 2.0 g of 1-bromo-2-chloroethane in 2 ml of methanol, and it is stirred for another 2.5 hours. Then, 4 ml of a 30% sodium methanolate solution is added, and it is refluxed for 19 hours. For working-up, it is diluted with diethyl ether, washed with water, dried on sodium sulfate, concentrated by evaporation in a vacuum and chromatographed on silica gel with hexane/ethyl acetate. 290 mg of vinyl-4,4,5,5,5-pentafluoropentylsulfide is obtained.

b) Vinyl-4,4,5,5,5-pentafluoropentylsulfone

A solution of 290 mg of vinyl-4,4,5,5,5-pentafluoropentyl sulfide in 3 ml of ethyl acetate is stirred with 0.81 ml of 30% hydrogen peroxide for 19 hours at room temperature. The reaction solution is diluted with diethyl ether, washed with water, dried on sodium sulfate, concentrated by evaporation in a vacuum and chromatographed on silica gel with hexane/ethyl acetate. 250 mg of vinyl-4,4,5,5,5-pentafluoropentyl sulfone with a melting point of 28–29° C. is obtained.

3-Chloropropyl-4,4,5,5,5-pentafluoropentyl sulfone

A solution of 114.2 g of 3-chloropropyl-4,4,5,5,5-pentafluoropentyl sulfide in 1.1 l of chloroform is mixed at 0° C. in portions with 98 g of 70% meta-chloroperbenzoic acid, and it is stirred for 0.5 hour. The reaction solution is washed with sodium hydrogen sulfite, sodium bicarbonate, common salt solution and water, dried on sodium sulfate, concentrated by evaporation in a vacuum and chromatographed on silica gel with dichloromethane/methanol. 70 g of 3-chloropropyl-4,4,5,5,5-pentafluoropentyl sulfone with a melting point of 74–76° C. is obtained.

Methyl-[3-(4,4,5,5,5-pentafluoropentylthio)-propyl]-amine a) 3-Iodopropyl-4,4,5,5,5-pentafluoropentyl sulfide A solution of 22.8 g of 3-chloropropyl-4,4,5,5,5-pentafluoropentyl sulfide in 500 ml of ethyl methyl ketone is stirred with 40 g of sodium iodide for 5 hours at a bath temperature of 100° C. under nitrogen. Then, it is evaporated to dryness in a vacuum, added to water, extracted three times with ethyl acetate, washed neutral and dried on sodium sulfate and concentrated by evaporation in a vacuum. 30.6 g of 3-iodopropyl-4,4,5,5,5-pentafluoropentyl sulfide is obtained.

b) Methyl-[3-(4,4,5,5,5-pentafluoropentylthio)-propyl]-amine 45 g of methylamine is condensed in a solution of 30.6 g of 3-iodopropyl-4,4,5,5,5-pentafluoropentyl sulfide in 200 ml of absolute tetrahydrofuran at a bath temperature of –78° C., and it is stirred for 1.5 hours at room temperature and for 4 hours at –60° C. in a pressurized reactor. To open the reactor, it is allowed to cool overnight to room temperature and then to –78° C. Then, it is allowed to reach room temperature, excess methylamine is evaporated, diluted with ethyl acetate, washed neutral, dried on sodium sulfate, concentrated by evaporation in a vacuum and chromatographed on silica gel with dichloromethane/methanol. 15.7 g of methyl-[3-(4,4,5,5,5-pentafluoropentylthio)-propyl]-amine is obtained as an oil.

3-Chloropropyl-4,4,5,5,5-pentafluoropentylsulfone

A solution of 5 g of 3-chloropropyl-4,4,5,5,5-pentafluoropentyl sulfide in 50 ml of acetic acid is stirred with 14 ml of 30% hydrogen peroxide for 19 hours at room temperature. The reaction solution is diluted with diethyl ether, washed with water, dried on sodium sulfate, concentrated by evaporation in a vacuum and chromatographed on silica gel with hexane/ethyl acetate. 5.1 g of 3-chloropropyl-4,4,5,5,5-pentafluoropentyl sulfone with a melting point of 61–62° C. is obtained.

Methyl-[3-(4,4,5,5,5-pentafluoropentanesulfonyl)-propyl]-amine a) 3-Iodopropyl-4,4,5,5,5-pentafluoropentane sulfone

A solution of 23.5 g of 3-chloropropyl-4,4,5,5,5-pentafluoropentanesulfone in 500 ml of ethyl methyl ketone is stirred with 40 g of sodium iodide for 5 hours at a bath temperature of 100° C. under nitrogen. Then, it is evaporated to dryness in a vacuum, added to water, extracted three times with ethyl acetate, washed neutral, and dried on sodium sulfate and concentrated by evaporation in a vacuum. 30.6 g of 3-iodopropyl-4,4,5,5,5-pentafluoropentanesulfone is obtained as crystals with a melting point of 88–89° C.

c) Methyl-[3-(4,4,5,5,5-pentafluoropentanesulfonyl)-propyl]-amine 44 g of methylamine is condensed at a bath temperature of −78° C. a solution of 23.5 g of 3-iodopropyl-4,4,5,5,5-pentafluoropentanesulfone in 200 ml of absolute tetrahydrofuran, and it is stirred for 1.5 hours at room temperature and for 4 hours at 60° C. in a pressurized reactor. To open the reactor, it is allowed to cool overnight to room temperature and then to −78° C. Then, it is allowed to reach room temperature, excess methylamine is evaporated, it is diluted with ethyl acetate, washed neutral, dried on sodium sulfate, concentrated by evaporation in a vacuum and chromatographed on silica gel with dichloromethane/methanol. 14.8 g of methyl-[3-(4,4,5,5,5-pentafluoropentanesulfonyl)-propyl]-amine is obtained as crystals with a melting point of 55–57° C.

What is claimed is:

1. 7α-(5-Methylaminopentyl)-estratrienes of general formula in which

R$^2$ stands for a hydrogen or fluorine atom,

R$^{17}$ stands for a hydrogen atom, a methyl or ethinyl group, n stands for 2, 3 or 4, and x stands for 0, 1 or 2.

2. Estratrienes according to claim 1, in which R$^2$ is a hydrogen atom.

3. Estratrienes according to claim 1, in which R$^2$ is a fluorine atom.

4. Estratrienes according to claim 1, in which R$^{17}$ stands for a hydrogen atom.

5. Estratrienes according to claim 1, in which R$^{17}$ stands for a methyl group.

6. Estratrienes according to claim 1, in which R$^{17}$ stands for an ethinyl group.

7. Estratrienes according to claim 1, in which n stands for 2.

8. Estratrienes according to claim 1, in which n stands for 3.

9. Estratrienes according to claim 1, in which n stands for 4.

10. Estratrienes according to claim 1, in which x stands for 0.

11. Estratrienes according to claim 1, in which x stands for 1.

12. Estratrienes according to claim 1, in which x stands for 2.

13. Estratrienes according to claim 1, namely

7α-{5-[N-Methyl-N-3-(4,4,5,5,5-pentafluoropentylthio)-propylamino]-pentyl}-estra-1,3,5(10)-triene-3,17β-diol 17α-methyl-7α-{5-[N-methyl-N-3-(4,4,5,5,5-pentafluoropentylthio)-propylamino]-pentyl}-estra-1,3,5(10)-triene-3,17β-diol 17α-ethinyl-7α-{5-[N-methyl-N-3-(4,4,5,5,5-pentafluoropentylthio)-propylamino]-pentyl}-estra-1,3,5(10)-triene-3,17β-diol 7α-{5-[N-methyl-N-2-(4,4,5,5,5-pentafluoropentanesulfonyl)-ethylamino]-pentyl}-estra-1,3,5(10)-triene-3,17β-diol 7α-{5-[N-methyl-N-3-(4,4,5,5,5-pentafluoropentanesulfonyl)-propylamino]-pentyl}-estra-1,3,5(10)-triene-3,17β-diol 2-fluoro-7α-{5-[N-methyl-N-3-(4,4,5,5,5-pentafluoropentylthio)-propylamino]-pentyl}-estra-1,3,5(10)-triene-3,17β-diol 7α-{5-[N-methyl-N-3-(4,4,5,5,5-pentafluoropentanesulfinyl)-propylamino]-pentyl}-estra-1,3,5(10)-triene-3,17β-diol 2-fluoro-17α-methyl-7α-{5-[N-methyl-N-3-(4,4,5,5,5-pentafluoropentylthio)-propylamino]-pentyl}-estra-1,3,5(10)-triene-3,17β-diol 2-fluoro-7α-{5-[N-methyl-3-(4,4,5,5,5-pentafluoropentanesulfinyl)-propylamino]-pentyl}-estra-1,3,5(10)-triene-3,17β-diol 2-fluoro-17α-methyl-7α-{5-[N-methyl-N-3-(4,4,5,5,5-pentafluoropentanesulfonyl)-propylamino]-pentyl}-estra-1,3,5(10)-triene-3,17β-diol 7α-{5-[N-methyl-N-4-(4,4,5,5,5-pentafluoropentylthio)-butylamino]-pentyl}-estra-1,3,5(10)-triene-3,17β-diol 7α-{5-[N-methyl-N-4-(4,4,5,5,5-pentafluoropentanesulfinyl)-butylamino]-pentyl}-estra-1,3,5(10)-triene-3,17β-diol 17α-methyl-7α-{5-[N-methyl-N-3-(4,4,5,5,5-pentafluoropentanesulfinyl)-propylamino]-pentyl}-estra-1,3,5(10)-triene-3,17β-diol 17α-methyl-7α-{5-[N-methyl-N-3-(4,4,5,5,5-pentafluoropentanesulfonyl)-propylamino]-pentyl}-estra-1,3,5(10)-triene-3,17β-diol 17α-ethinyl-7α-{5-[N-methyl-N-3-(4,4,5,5,5-pentafluoropentanesulfonyl)-propylamino]-pentyl}-estra-1,3,5(10)-triene-3,17β-diol.

14. A pharmaceutical preparation comprising at least one compound according to claim 1 and a pharmaceutically compatible vehicle.

15. A method of inhibiting growth of estrogen-dependent human breast neoplasm cells comprising administering a compound of claim 1.

16. A method according to claim 15, comprising administering 0.1–25 mg/kg of body weight, per day, of said compound.

* * * * *

UNITED STATES PATENT AND TRADEMARK OFFICE
CERTIFICATE OF CORRECTION

PATENT NO. : 6,288,051 B1
DATED : September 11, 2001
INVENTOR(S) : Dieter Bittler et al.

It is certified that error appears in the above-identified patent and that said Letters Patent is hereby corrected as shown below:

Title page,
Item [63], Related U.S. Application Data, delete "Nov. 4, 1998" and insert -- May 26, 1997 --; and after "abandoned" insert -- , and provisional application Serial No. 60/029,951, filed November 8, 1996 --

Column 1,
Line 9, after the title, insert the following:

-- This application claims priority of prior provisional application Serial No. 60/029,951, filed November 8, 1996. This application is a continuation application of parent application Serial No. 09/194,120, filed November 23, 1998. --

Signed and Sealed this

Twenty-second Day of June, 2004

JON W. DUDAS
*Acting Director of the United States Patent and Trademark Office*